(12) United States Patent
Sims

(10) Patent No.: US 7,285,648 B1
(45) Date of Patent: Oct. 23, 2007

(54) IL-1 DELTA DNA AND POLYPEPTIDES

(75) Inventor: John E. Sims, Seattle, WA (US)

(73) Assignee: Immunex Corporation, Seattle, WA (US)

( * ) Notice: Subject to any disclaimer, the term of this patent is extended or adjusted under 35 U.S.C. 154(b) by 58 days.

(21) Appl. No.: 09/612,921

(22) Filed: Jul. 10, 2000

Related U.S. Application Data

(63) Continuation of application No. PCT/US99/00514, filed on Jan. 8, 1999.

(60) Provisional application No. 60/087,393, filed on Jun. 1, 1998, provisional application No. 60/071,074, filed on Jan. 9, 1998.

(51) Int. Cl.
*C07H 21/02* (2006.01)
*C07H 21/04* (2006.01)
*G01N 33/567* (2006.01)
*C12Q 1/68* (2006.01)

(52) U.S. Cl. .................... 536/23.1; 536/24.3; 436/504; 435/6

(58) Field of Classification Search ............ 435/69.52, 435/69.5, 252.3; 536/320.1, 23.5, 235
See application file for complete search history.

(56) References Cited

U.S. PATENT DOCUMENTS

| | | |
|---|---|---|
| 6,337,072 B1 | 1/2002 | Ford et al. |
| 6,541,623 B1* | 4/2003 | Ford et al. ................. 536/24.3 |
| 2002/0119130 A1* | 8/2002 | Eaton et al. ............... 424/94.1 |

FOREIGN PATENT DOCUMENTS

| | | |
|---|---|---|
| WO | WO98 47921 | 10/1998 |
| WO | WO98/47921 | 10/1998 |
| WO | WO99/51744 | 10/1999 |
| WO | WO 00/08045 | 2/2000 |
| WO | WO 00/20595 | 4/2000 |
| WO | WO 00/39297 | 7/2000 |
| WO | WO 01/02571 | 1/2001 |
| WO | WO 01/05974 | 1/2001 |
| WO | WO 01/16318 A2 | 3/2001 |

OTHER PUBLICATIONS

Mikayama et al. Proc. Natl. Acad. Sci. USA vol. 90, pp. 10056-10060. Molecular cloning and functional expression of a cDNA encoding glycosylation-inhibiting factor, 1993.*
Voet et al. Biochemistry, John Wiley & Sons, Inc. pp. 126-128, and 228-234, 1990.*
Skolnick J and Fetrow JS. 2000, Trends in Bitech., vol. 18, pp. 34-39. from genes to protein structure and function: novel applications of computtional apporaches in the genomic era.*
Bork P., 2000, Genome research, vol. 10, pp. 390-400. Pwers and pitfalls in sequence analysis: the 70% hurdle.*
Map view of human chromosome 2q11-2q12 (Entrez).*
Smith et al. 2000, J Biol Chem. vol. 275: pp. 1169-1175. Four members Expand the interleukin—1 superfamily.*
Database EMBL, Entry MM 2052, Accession No. W08205, Apr. 27, 1996, XP002098884.
Database EMBL., Entry MM59411, Accession No. W20594, May 8, 1996, XP002098885.
Dinarello, Cytokine and Growth Factor Reviews, 8(4):253-265 (1997).

* cited by examiner

*Primary Examiner*—Olga N. Chernyshev
(74) *Attorney, Agent, or Firm*—Finnegan, Henderson, Farabow, Garrett & Dunner, LLP

(57) ABSTRACT

DNA encoding IL-1 delta polypeptides and methods for using the DNA and encoded polypeptides are disclosed.

1 Claim, No Drawings

SEQUENCE LISTING

<160> NUMBER OF SEQ ID NOS: 11

<210> SEQ ID NO 1
<211> LENGTH: 468

-continued

```
<212> TYPE: DNA
<213> ORGANISM: Mus musculus

<400> SEQUENCE: 1
atgatggttc tgagtggggc actatgcttc cgaatgaagg attcagcctt gaaggtactg      60
tatctgcaca ataaccagct gctggctgga ggactgcacg cagagaaggt cattaaaggt     120
gaggagatca gtgttgtccc aaatcgggca ctggatgcca gtctgtcccc tgtcatcctg     180
ggcgttcaag gaggaagcca gtgcctatct tgtgggacag agaaagggcc aattctgaaa     240
cttgagccag tgaacatcat ggagctctac ctcggggcca aggaatcaaa gagcttcacc     300
ttctaccggc gggatatggg tcttacctcc agcttcgaat ccgctgccta cccaggctgg     360
ttcctctgca cctcaccgga agctgaccag cctgtcaggc tcactcagat ccctgaggac     420
cccgcctggg atgctcccat cacagacttc tactttcagc agtgtgac                 468

<210> SEQ ID NO 2
<211> LENGTH: 156
<212> TYPE: PRT
<213> ORGANISM: Mus musculus

<400> SEQUENCE: 2

Met Met Val Leu Ser Gly Ala Leu Cys Phe Arg Met Lys Asp Ser Ala
1               5                   10                  15

Leu Lys Val Leu Tyr Leu His Asn Asn Gln Leu Leu Ala Gly Gly Leu
            20                  25                  30

His Ala Glu Lys Val Ile Lys Gly Glu Glu Ile Ser Val Val Pro Asn
        35                  40                  45

Arg Ala Leu Asp Ala Ser Leu Ser Pro Val Ile Leu Gly Val Gln Gly
    50                  55                  60

Gly Ser Gln Cys Leu Ser Cys Gly Thr Glu Lys Gly Pro Ile Leu Lys
65                  70                  75                  80

Leu Glu Pro Val Asn Ile Met Glu Leu Tyr Leu Gly Ala Lys Glu Ser
                85                  90                  95

Lys Ser Phe Thr Phe Tyr Arg Arg Asp Met Gly Leu Thr Ser Ser Phe
            100                 105                 110

Glu Ser Ala Ala Tyr Pro Gly Trp Phe Leu Cys Thr Ser Pro Glu Ala
        115                 120                 125

Asp Gln Pro Val Arg Leu Thr Gln Ile Pro Glu Asp Pro Ala Trp Asp
    130                 135                 140

Ala Pro Ile Thr Asp Phe Tyr Phe Gln Gln Cys Asp
145                 150                 155

<210> SEQ ID NO 3
<211> LENGTH: 468
<212> TYPE: DNA
<213> ORGANISM: Homo sapiens

<400> SEQUENCE: 3
atggtcctga gtggggcgct gtgcttccga atgaaggact cggcattgaa ggtgctttat      60
ctgcataata accagcttct agctggaggg ctgcatgcag ggaaggtcat taaggtgaa     120 gagatcagcg tggtccccaa tcggtggctg atgccagcc tgtcccccgt catcctgggt     180
gtccagggtg aagccagtg cctgtcatgt ggggtgggc aggagccgac tctaacacta     240
gagccagtga acatcatgga gctctatctt ggtgccaagg aatccaagag cttcaccttc     300
taccggcggg acatggggct cacctccagc ttcgagtcgg ctgcctaccc gggctggttc     360
```

```
ctgtgcacgg tgcctgaagc cgatcagcct gtcagactca cccagcttcc cgagaatggt    420
ggctggaatg cccccatcac agacttctac ttccagcagt gtgactag                468
```

<210> SEQ ID NO 4
<211> LENGTH: 155
<212> TYPE: PRT
<213> ORGANISM: Homo sapiens

<400> SEQUENCE: 4

```
Met Val Leu Ser Gly Ala Leu Cys Phe Arg Met Lys Asp Ser Ala Leu
1               5                   10                  15

Lys Val Leu Tyr Leu His Asn Asn Gln Leu Leu Ala Gly Gly Leu His
            20                  25                  30

Ala Gly Lys Val Ile Lys Gly Glu Glu Ile Ser Val Val Pro Asn Arg
        35                  40                  45

Trp Leu Asp Ala Ser Leu Ser Pro Val Ile Leu Gly Val Gln Gly Gly
    50                  55                  60

Ser Gln Cys Leu Ser Cys Gly Val Gly Gln Glu Pro Thr Leu Thr Leu
65                  70                  75                  80

Glu Pro Val Asn Ile Met Glu Leu Tyr Leu Gly Ala Lys Glu Ser Lys
                85                  90                  95

Ser Phe Thr Phe Tyr Arg Arg Asp Met Gly Leu Thr Ser Ser Phe Glu
            100                 105                 110

Ser Ala Ala Tyr Pro Gly Trp Phe Leu Cys Thr Val Pro Glu Ala Asp
        115                 120                 125

Gln Pro Val Arg Leu Thr Gln Leu Pro Glu Asn Gly Gly Trp Asn Ala
    130                 135                 140

Pro Ile Thr Asp Phe Tyr Phe Gln Gln Cys Asp
145                 150                 155
```

<210> SEQ ID NO 5
<211> LENGTH: 8
<212> TYPE: PRT
<213> ORGANISM: Artificial
<220> FEATURE:
<223> OTHER INFORMATION: FLAG peptide

<400> SEQUENCE: 5

```
Asp Tyr Lys Asp Asp Asp Asp Lys
1               5
```

<210> SEQ ID NO 6
<211> LENGTH: 27
<212> TYPE: PRT
<213> ORGANISM: Artificial
<220> FEATURE:
<223> OTHER INFORMATION: leucine zipper peptide

<400> SEQUENCE: 6

```
Pro Asp Val Ala Ser Leu Arg Gln Gln Val Glu Ala Leu Gln Gly Gln
1               5                   10                  15

Val Gln His Leu Gln Ala Ala Phe Ser Gln Tyr
            20                  25
```

<210> SEQ ID NO 7
<211> LENGTH: 33
<212> TYPE: PRT
<213> ORGANISM: Artificial
<220> FEATURE:
<223> OTHER INFORMATION: leucine zipper peptide -continued

```
<400> SEQUENCE: 7

Arg Met Lys Gln Ile Glu Asp Lys Ile Glu Glu Ile Leu Ser Lys Ile
1               5                   10                  15

Tyr His Ile Glu Asn Glu Ile Ala Arg Ile Lys Lys Leu Ile Gly Glu
            20                  25                  30

Arg

<210> SEQ ID NO 8
<211> LENGTH: 26
<212> TYPE: DNA
<213> ORGANISM: Artificial
<220> FEATURE:
<223> OTHER INFORMATION: oligonucleotide PCR primer

<400> SEQUENCE: 8
gggagtctac accctgtgga gctcaa                                            26

<210> SEQ ID NO 9
<211> LENGTH: 26
<212> TYPE: DNA
<213> ORGANISM: Artificial
<220> FEATURE:
<223> OTHER INFORMATION: oligonucleotide PCR primer

<400> SEQUENCE: 9
ctgctggaag tagaagtctg tgatgg                                            26

<210> SEQ ID NO 10
<211> LENGTH: 30
<212> TYPE: DNA
<213> ORGANISM: Artificial
<220> FEATURE:
<223> OTHER INFORMATION: oligonucleotide PCR primer

<400> SEQUENCE: 10
ggagctcaag atggtcctga gtgggcgct                                         30

<210> SEQ ID NO 11
<211> LENGTH: 28
<212> TYPE: DNA
<213> ORGANISM: Artificial
<220> FEATURE:
<223> OTHER INFORMATION: oligonucleotide PCR primer

<400> SEQUENCE: 11
gcattccagc caccattctc gggaagct                                          28
```

IL-1 DELTA DNA AND POLYPEPTIDES

This application is a Continuation of International Application No. PCT/US99/00514, filed Jan. 8, 1999, and claims the benefit of U.S. Provisional Application No. 60/071,074, filed Jan. 9, 1998, and U.S. Provisional Application No. 60/087,393, filed Jun. 1, 1998, the content of all of which is incorporated herein by reference.

BACKGROUND OF THE INVENTION

1. Field of the Invention

The invention is directed to purified and isolated novel IL-1 delta polypeptides and fragments thereof, the nucleic acids encoding such polypeptides, processes for production of recombinant forms of such polypeptides, antibodies generated against these polypeptides, fragmented peptides derived from these polypeptides, and uses thereof.

2. Description of Related Art

1. IL-1 and IL-1R

Interleukin-1 (IL-1) is a member of a large group of cytokines whose primary function is to mediate immune and inflammatory responses. Members of the IL-1 ligand family include IL-1 alpha (IL-1α), IL-1 beta (IL-1β), IL-1 receptor antagonist (IL-1ra), and IL-18 (previously known as IGIF and sometimes IL-1 gamma), IL-1 epsilon (IL-1ε), and IL-1 zeta (IL-1ζ). IL-1 that is secreted by macrophages is actually a mixture of mostly IL-1β and some IL-1α (Abbas et al., 1994). IL-1α and IL-1β, which are first produced as 33 kD precursors that lack a signal sequence, are further processed by proteolytic cleavage to produce secreted active forms, each about 17 kD. Additionally, the 33 kD precursor of IL-1α is also active. Both forms of IL-1 are the products of two different genes located on chromosome 2. Although the two forms are less than 30 percent homologous to each other, they both bind to the same receptors and have similar activities.

IL-1ra, a biologically inactive form of IL-1, is structurally homologous to IL-1 and binds to the same receptors. Additionally, IL-1ra is produced with a signal sequence which allows for efficient secretion into the extracellular region where it competitively competes with IL-1 (Abbas et al., 1994).

The IL-1 type I receptor mediates the biological effects of IL-1. Activities attributed to IL-1α and IL-1β include induction of inflammatory cytokines and other inflammatory responses including prostaglandins, nitric oxide, metalloproteinases, adhesion molecules, acute phase proteins, hematopoiesis, fever, bone resorption, and Th2 cell growth and differentiation.

IL-1 has been implicated in chronic inflammatory diseases, such as rheumatoid arthritis and inflammatory bowel disease. There is increasing evidence that IL-1 plays a role in osteoporosis. All of these activities are initiated by the signaling function of the cytoplasmic portion of the type I IL-1R.

IL-18 is a homolog of IL-1α and IL-1β and binds to and signals through a receptor comprised of the IL-1 family members IL-1 receptor related protein 1, IL-1 Rrp1 (See Parnet et al., *J. Biol. Chem* 271:3967, 1996, and Torigoe et al., *J. Biol. Chem* 272:25737, 1997), and AcPL (See U.S. Provisional Patent Application 60/072,301 of John E. SIMS and Teresa L. BORN for ACPL DNA and Polypeptides filed Jan. 23, 1998, and U.S. Provisional Application No. 60/078,835, of John E. SIMS and Teresa L. BORN for ACPL DNA and Polypeptides filed Mar. 20, 1998, both of which are hereby incorporated by reference). IL-18 acts as a stimulator of Th1 cell growth and differentiation, and is a potent inducer of γ-interferon production from Th1 cells. It enhances NK cell killing activity. It has been implicated in septic shock, liver destruction, inflammatory bowel disease, and diabetes.

The IL-1 ligands bind to two IL-1 receptors, which are members of the Ig superfamily. IL-1 receptors include the 80 kDa type I receptor (IL-1RI), and a 68 kDa type II receptor (IL-1RII). IL-1 ligands can also bind to a soluble proteolytic fragment of IL-1RII (sIL-1RII) (Colotta et al., 1993).

IL-1 receptors are members of the large Ig superfamily of cytokine receptors, many of which mediate the response of immune system cells, in particular lymphocytes. In recent years, members of the ligands that bind to these receptors have been discovered at an accelerated pace. The increase in the number of known IL-1 ligands has been largely due to the advent of gene cloning and sequencing techniques. Amino acid sequences deduced from nucleotide sequences are considered to represent IL-1 ligands if they share homology with other known IL-1 ligands.

The major source of IL-1 is the activated macrophage or mononuclear phagocyte. Other cells that produce IL-1 include epithelial and endothelial cells (Abbas et al., 1994). IL-1 secretion from macrophages occurs after the macrophage encounters and ingests gram-negative bacteria. Such bacteria contain lipopolysaccharide (LPS) molecules, also known as endotoxin, in the bacterial cell wall. LPS molecules are the active components that stimulate macrophages to produce tumor necrosis factor (TNF) and IL-1. In this case, IL-1 is produced in response to LPS and TNF production. At low concentrations, LPS stimulates macrophages and activates B-cells and other host responses needed to eliminate the bacterial infection; however, at high concentrations, LPS can cause severe tissue damage, shock, and even death.

The biological functions of IL-1 include activating vascular endothelial cells and lymphocytes, local tissue destruction, and fever (Janeway et al., 1996). At low levels, IL-1 stimulates macrophages and vascular endothelial cells to produce IL-6, upregulates molecules on the surface of vascular endothelial cells to increase leukocyte adhesion, and indirectly activates inflammatory leukocytes by stimulating mononuclear phagocytes and other cells to produce certain chemokines that activate inflammatory leukocytes. Additionally, IL-1 is involved in other inflammatory responses such as induction of prostaglandins, nitric oxide synthetase, and metalloproteinases. These IL-1 functions are crucial during low level microbial infections. However, if the microbial infection escalates, IL-1 acts systemically by inducing fever, stimulating mononuclear phagocytes to produce IL-1 and IL-6, increasing the production of serum proteins from hepatocytes, and activating the coagulation system. Additionally, IL-1 does not cause hemorrhagic necrosis of tumors or suppress bone marrow stem cell division, and IL-1 is lethal to humans at high concentrations.

IL-1 mediated cellular signaling often involves a molecular activation cascade, during which a receptor propagates a ligand-receptor mediated signal by specifically activating intracellular kinases which phosphorylate target substrates. IL-1 mediated cellular signaling may result in the activation of the transcription factors NFkB and AP1 (Stylianou et al., *Int. J. Biochem Cell Biol.* 30: 1075-1079, 1998), the protein kinases Jun N-terminal kinase and p38 map kinase (O'Neil et al., *J. Leukoc. Biol.* 63:650-657, 1998), the enzymes COX-2 leading to prostaglandin production (Crofford, *J. Rheumatol.* 24 Suppl. 49:15-19, 1997) and iNOS leading to nitric oxide production (Alexander, *Nutrition* 14: 376-90, 1998) and inflammation in general.

Given the important function of IL-1 and IL-1R, there is a need in the art for additional members of the IL-1 ligand family. Despite the growing body of knowledge, there is still a need in the art for the identity and function of proteins involved in cellular and immune responses.

2. Protein Identification

In another aspect, the identification of the primary structure, or sequence, of an unknown protein is the culmination of an arduous process of experimentation. In order to identify an unknown protein, the investigator can rely upon a comparison of the unknown protein to known peptides using a variety of techniques known to those skilled in the art. For instance, proteins are routinely analyzed using techniques such as electrophoresis, sedimentation, chromatography, sequencing and mass spectrometry.

In particular, comparison of an unknown protein to polypeptides of known molecular weight allows a determination of the apparent molecular weight of the unknown protein (T. D. Brock and M. T. Madigan, *Biology of Microorganisms* 76-77 (Prentice Hall, 6d ed. 1991)). Protein molecular weight standards are commercially available to assist in the estimation of molecular weights of unknown protein (New England Biolabs Inc. Catalog: 130-131, 1995; J. L. Hartley, U.S. Pat. No. 5,449,758). However, the molecular weight standards may not correspond closely enough in size to the unknown protein to allow an accurate estimation of apparent molecular weight. The difficulty in estimation of molecular weight is compounded in the case of proteins that are subjected to fragmentation by chemical or enzymatic means, modified by post-translational modification or processing, and/or associated with other proteins in non-covalent complexes.

In addition, the unique nature of the composition of a protein with regard to its specific amino acid constituents results in unique positioning of cleavage sites within the protein. Specific fragmentation of a protein by chemical or enzymatic cleavage results in a unique "peptide fingerprint" (D. W. Cleveland et al., *J. Biol. Chem.* 252:1102-1106,1977; M. Brown et al., *J. Gen. Virol.* 50:309-316, 1980). Consequently, cleavage at specific sites results in reproducible fragmentation of a given protein into peptides of precise molecular weights. Furthermore, these peptides possess unique charge characteristics that determine the isoelectric pH of the peptide. These unique characteristics can be exploited using a variety of electrophoretic and other techniques (T. D. Brock and M. T. Madigan, *Biology of Microorganisms* 76-77 (Prentice Hall, 6d ed. 1991)).

Fragmentation of proteins is further employed for amino acid composition analysis and protein sequencing (P. Matsudiara, *J. Biol. Chem.* 262:10035-10038, 1987; C. Eckerskom et al., *Electrophoresis* 1988,9:830-838, 1988), particularly the production of fragments from proteins with a "blocked" N-terminus. In addition, fragmented proteins can be used for immunization, for affinity selection (R. A. Brown, U.S. Pat. No. 5,151,412), for determination of modification sites (e.g. phosphorylation), for generation of active biological compounds (T. D. Brock and M. T. Madigan, *Biology of Microorganisms* 300-301 (Prentice Hall, 6d ed. 1991)), and for differentiation of homologous proteins (M. Brown et al., *J. Gen. Virol.* 50:309-316,1980).

In addition, when a peptide fingerprint of an unknown protein is obtained, it can be compared to a database of known proteins to assist in the identification of the unknown protein using mass spectrometry (W. J. Henzel et al., *Proc. Natl. Acad. Sci. USA* 90:5011-5015, 1993; D. Fenyo et al., *Electrophoresis* 19:998-1005, 1998). A variety of computer software programs to facilitate these comparisons are accessible via the Internet, such as Protein Prospector (Internet site: prospector.uscf.edu), Multildent (Internet site: www.expasy.ch/sprot/multiident.html), PeptideSearch (Internet site: www.mann.embl-heiedelberg.de . . . deSearch/FR PeptideSearch Form.html), and ProFound (Internet site: www.chait sgi.rockefeller.edu/cgi bin/prot id frag.html). These programs allow the user to specify the cleavage agent and the molecular weights of the fragmented peptides within a designated tolerance. The programs compare these molecular weights to protein molecular weight information stored in databases to assist in determining the identity of the unknown protein. Accurate information concerning the number of fragmented peptides and the precise molecular weight of those peptides is required for accurate identification. Therefore, increasing the accuracy in determining the number of fragmented peptides and their molecular weight should result in enhanced likelihood of success in the identification of unknown proteins.

In addition, peptide digests of unknown proteins can be sequenced using tandem mass spectrometry (MS/MS) and the resulting sequence searched against databases (J. K. Eng, et al., *J. Am. Soc. Mass Spec.* 5:976-989 (1994); M. Mann and M. Wilm, *Anal. Chem.* 66:4390-4399 (1994); J. A. Taylor and R. S. Johnson, *Rapid Comm. Mass Spec.* 11:1067-1075 (1997)). Searching programs that can be used in this process exist on the Internet, such as Lutefisk 97 (Internet site www.Isbc.com:70/Lutefisk97.html), and the Protein Prospector, Peptide Search and ProFound programs described above. Therefore, adding the sequence of a gene and its predicted protein sequence and peptide fragments to a sequence database can aid in the identification of unknown proteins using tandem mass spectrometry.

Thus, there exists a need in the art for polypeptides suitable for use in peptide fragmentation studies, for use in molecular weight measurements, and for use in protein sequencing using tandem mass spectrometry.

SUMMARY OF THE INVENTION

The invention aids in fulfilling these various needs in the art by providing isolated IL-1 delta nucleic acids and polypeptides encoded by these nucleic acids. Particular embodiments of the invention are directed to an isolated IL-1 delta nucleic acid molecule comprising the murine DNA sequence of SEQ ID NO:1 and the human DNA sequence of SEQ ID NO:3 and an isolated IL-1 delta nucleic acid molecule encoding the corresponding amino acid sequences of SEQ ID NO:2 or SEQ ID NO:4, as well as nucleic acid molecules complementary to these sequences. Both single-stranded and double-stranded RNA and DNA nucleic acid molecules are encompassed by the invention, as well as nucleic acid molecules that hybridize to a denatured, double-stranded DNA comprising all or a portion of SEQ ID NO:1 or SEQ ID NO:3 Also encompassed are isolated nucleic acid molecules that are derived by in vitro mutagenesis of nucleic acid molecules comprising sequences of SEQ ID NO:1 or SEQ ID NO:3, that are degenerate from nucleic acid molecules comprising sequences of SEQ ID NO:1 or SEQ ID NO:3, and that are allelic variants of DNA of the invention. The invention also encompasses recombinant vectors that direct the expression of these nucleic acid molecules and host cells stably or transiently transformed or transfected with these vectors.

In addition, the invention encompasses methods of using the nucleic acids noted above to identify nucleic acids encoding proteins having IL-1 delta activity; to identify human chromosome 2; to map genes on human chromosome 2, to identify genes associated with certain diseases, syndromes, or other human conditions associated with human chromosome 2; and to study cell signal transduction and the IL-1 delta system.

The invention also encompasses the use of sense or antisense oligonucleotides from the nucleic acid of SEQ ID NO:1 or SEQ ID NO:3 to inhibit the expression of the polynucleotide encoded by the IL-1 delta gene.

The invention also encompasses isolated polypeptides and fragments thereof encoded by these nucleic acid molecules including soluble polypeptide portions of SEQ ID NO:2 or SEQ ID NO:4. The invention further encompasses methods for the production of these polypeptides, including culturing a host cell under conditions promoting expression and recovering the polypeptide from the culture medium. Especially, the expression of these polypeptides in bacteria, yeast, plant, insect, and animal cells is encompassed by the invention.

In general, the polypeptides of the invention can be used to study cellular processes such as immune regulation, cell proliferation, cell death, cell migration, cell-to-cell interaction, and inflammatory responses. In addition, these polypeptides can be used to identify proteins associated with IL-1 delta ligands and IL-1 delta receptors.

In addition, the invention includes assays utilizing these polypeptides to screen for potential inhibitors of activity associated with polypeptide counter-structure molecules, and methods of using these polypeptides as therapeutic agents for the treatment of diseases mediated by IL-1 delta polypeptide counter-structure molecules. Further, methods of using these polypeptides in the design of inhibitors thereof are also an aspect of the invention.

The invention further provides a method for using these polypeptides as molecular weight markers that allow the estimation of the molecular weight of a protein or a fragmented protein, as well as a method for the visualization of the molecular weight markers of the invention thereof using electrophoresis. The invention further encompasses methods for using the polypeptides of the invention as markers for determining the isoelectric point of an unknown protein, as well as controls for establishing the extent of fragmentation of a protein.

Further encompassed by this invention are kits to aid in these determinations.

Further encompassed by this invention is the use of the IL-1 delta nucleic acid sequences, predicted amino acid sequences of the polypeptide or fragments thereof, or a combination of the predicted amino acid sequences of the polypeptide and fragments thereof for use in searching an electronic database to aid in the identification of sample nucleic acids and/or proteins.

Isolated polyclonal or monoclonal antibodies that bind to these polypeptides are also encompassed by the invention, in addition the use of these antibodies to aid in purifying the IL-1 delta polypeptide.

The invention also encompasses isolated polypeptides encoded by these nucleic acid molecules, including isolated polypeptides having a molecular weight of approximately 17 kD as determined by SDS-PAGE and isolated polypeptides in non-glycosylated form.

The invention further encompasses the fragmented peptides produced from IL-1 delta polypeptides by chemical or enzymatic treatment. In addition, forms of IL-1 delta polypeptide molecular weight markers and fragmented peptides thereof, wherein at least one of the sites necessary for fragmentation by chemical or enzymatic means has been mutated, are an aspect of the invention.

DETAILED DESCRIPTION OF THE INVENTION

A cDNA encoding mouse IL-1 delta polypeptide has been isolated and is disclosed in SEQ ID NO:1.

ATGATGGTTCTGAGTGGGGCACTATGCTTCCGAATGAAGGATTCAGCCTT

GAAGGTACTGTATCTGCACAATAACCAGCTGCTGGCTGGAGGACTGCACG

CAGAGAAGGTCATTAAAGGTGAGGAGATCAGTGTTGTCCCAAATCGGGCA

CTGGATGCCAGTCTGTCCCCTGTCATCCTGGGCGTTCAAGGAGGAAGCCA

GTGCCTATCTTGTGGGACAGAGAAAGGGCCAATTCTGAAACTTGAGCCAG

TGAACATCATGGAGCTCTACCTCGGGGCCAAGGAATCAAAGAGCTTCACC

TTCTACCGGCGGGATATGGGTCTTACCTCCAGCTTCGAATCCGCTGCCTA

CCCAGGCTGGTTCCTCTGCACCTCACCGGAAGCTGACCAGCCTGTCAGGC

TCACTCAGATCCCTGAGGACCCCGCCTGGGATGCTCCCATCACAGACTTC

TACTTTCAGCAGTGTGAC (SEQ ID NO:1)

A cDNA encoding human IL-1 delta polypeptide has been isolated and is disclosed in SEQ ID NO:3.

ATGGTCCTGA GTGGGCGCT GTGCTTCCGA ATGAAGGACT CGGCATTGAA

GGTGCTTTAT CTGCATAATA ACCAGCTTCT AGCTGGAGGG CTGCATGCAG

GGAAGGTCAT TAAAGGTGAA GAGATCAGCG TGGTCCCCAA TCGGTGGCTG

GATGCCAGCC TGTCCCCCGT CATCCTGGGT GTCCAGGGTG GAAGCCAGTG

CCTGTCATGT GGGGTGGGGC AGGAGCCGAC TCTAACACTA GAGCCAGTGA

ACATCATGGA GCTCTATCTT GGTGCCAAGG AATCCAAGAG CTTCACCTTC

TACCGGCGGG ACATGGGGCT CACCTCCAGC TTCGAGTCGG CTGCCTACCC

GGGCTGGTTC CTGTGCACGG TGCCTGAAGC CGATCAGCCT GTCAGACTCA

CCCAGCTTCC CGAGAATGGT GGCTGGAATG CCCCCATCAC AGACTTCTAC

TTCCAGCAGT GTGACTAG (SEQ ID NO:3)

This discovery of the cDNAs encoding IL-1 delta polypeptides enables construction of expression vectors comprising nucleic acid sequences encoding IL-1 delta polypeptides; host cells transfected or transformed with the expression vectors; biologically active IL-1 delta polypeptides and IL-1 delta molecular weight markers as isolated and purified proteins; and antibodies immunoreactive with IL-1 delta polypeptides. In addition, understanding of the mechanism by which IL-1 delta functions in IL-1 signaling enables the design of assays to detect inhibitors of IL-1 activity.

Mouse IL-1 delta DNA was originally seen as a partial EST clone in the public databases (mouse EST W08205). The DNA sequence of the entire IMAGE clone was determined. The sequence of EST clones W08205 and W20594 overlaps with nucleotides of mouse IL-1 delta DNA (SEQ ID NO:1). No other homologous EST sequences have been identified.

Murine mRNA expression has been demonstrated in spleen cells stimulated with CD40L. The expression is further augmented by stimulation with both lipopolysaccharide (LPS) and CD40L. mRNA expression has been demonstrated in a mouse macrophage line (RAW) stimulated with LPS and in both the mouse placenta and yolk sac of a 14 day embryo. The cDNA has been detected in a kidney cDNA library.

Human IL-1 delta RNA expression can be detected in lymph node, thymus, tonsil, brain, placenta, lung, skeletal muscle, prostate, and testis.

A preferred polypeptide encoded by SEQ ID NO:1 is set forth below:

MMVLSGALCFRMKDSALKVLYLHNNQLLAGGLHAEKVIKGEEISVVPNRA

LDASLSPVILGVQGGSQCLSCGTEKGPILKLEPVNIMELYLGAKESKSFT

FYRRDMGLTSSFESAAYPGWFLCTSPEADQPVRLTQIPEDPAWDAPITDF

YFQQCD (SEQ ID NO:2)

A preferred polypeptide encoded by SEQ ID NO:3 is set forth below:

```
MVLSGALCFR MKDSALKVLY LHNNQLLAGG LHAGKVIKGE EISVVPRNWL

DASLSPVILG VQGGSQCLSC GVGQEPTLTL EPVNIMELYL GAKESKSFTF

YRRDMGLTSS FESAAYPGWF LCTVPEADQP VRLTQLPENG GWNAPITDFY

FQQCD (SEQ ID NO:4)
```

Mouse IL-1 delta polypeptide is homologous to the mature portion of the IL-1 family members (IL-1α, IL-1β, IL-1ra, and IL-18). The mouse IL-1 delta amino acid sequence was compared to the mature forms of the other mouse IL-1 family members using the UWGCG computer program "gap." Mouse IL-1 delta polypeptide exhibited 23% identity with IL-1α, 30% identity with IL-1β, 48% identity with IL-1ra, and 18% identity with IL-18.

The human IL-1 delta amino acid sequence was compared to the mature forms of the other human IL-1 family members. Human IL-1 delta polypeptide exhibited little identity with IL-1α, 29% identity with IL-1β, 50% identity with IL-1ra, little identity with IL-18, 31% identity with IL-1 epsilon, and 34% with IL-1 zeta, as determined by the UWGCG program GAP, using a gap creation penalty of 12 and a gap extension penalty of 4.

Unlike IL-1α, IL-1β, and IL-18, the IL-1 delta polypeptide does not contain a "pro" region (an N-terminal segment, which is removed by proteolytic processing). Unlike IL-1ra, IL-1 delta polypeptide does not contain a signal peptide.

A secreted version of mouse IL-1 delta was generated by fusing the IL-1ra signal peptide to the coding region. Inefficient protein production was found in the COS and CV1/EBNA mammalian systems and in bacterial systems.

Human IL-1 delta is secreted with moderate efficiency from transfected COS or CV-1/EBNA cells, even in the absence of an exogenous signal peptide. Sequencing of the N-terminus indicates that no cleavage has occurred. Therefore, native IL-1 delta can be secreted from the cell even in the absence of a signal peptide or a "pro" region.

A soluble version of the IL-1 delta receptor IL-1 delta may acts as an antagonist of other, active cytokines, in the same way that IL-1ra is an antagonist of the actions of IL-1 alpha and IL-1 beta.

The discovery of the nucleic acids of the invention enables the construction of expression vectors comprising nucleic acid sequences encoding polypeptides; host cells transfected or transformed with the expression vectors; isolated and purified biologically active polypeptides and fragments thereof; the use of the nucleic acids or oligonucleotides thereof as probes to identify nucleic acid encoding proteins having IL-1 delta activity. The invention also provides for the use of the nucleic acids or oligonucleotides thereof to identify human chromosome 2, to map genes on human chromosome 2, and to identify genes associated with certain diseases, syndromes or other human conditions associated with human chromosome 2, particularly with region 2q11-12, including glaucoma, ectodermal dysplasia, insulin-dependent diabetes mellitus, wrinkly skin syndrome, T-cell leukemia/lymphoma, and tibial muscular dystrophy. In another aspect, the invention describes the use of single-stranded sense or antisense oligonucleotides from the nucleic acids to inhibit expression of polynucleotide encoded by the IL-1 delta gene. The invention also enables the use of such polypeptides and soluble fragments as molecular weight markers, as controls for peptide fragmentation, as well as kits comprising these reagents. Finally, the invention provides for the use of such polypeptides and fragments thereof to generate antibodies, and the use of antibodies to purify the IL-1 delta polypeptide.

Nucleic Acid Molecules

In a particular embodiment, the invention relates to certain isolated nucleotide sequences that are free from contaminating endogenous material. A "nucleotide sequence" refers to a polynucleotide molecule in the form of a separate fragment or as a component of a larger nucleic acid construct. The nucleic acid molecule has been derived from DNA or RNA isolated at least once in substantially pure form and in a quantity or concentration enabling identification, manipulation, and recovery of its component nucleotide sequences by standard biochemical methods (such as those outlined in Sambrook et al., *Molecular Cloning: A*

*Laboratory Manual,* 2nd sed., Cold Spring Harbor Laboratory, Cold Spring Harbor, N.Y. (1989)). Such sequences are preferably provided and/or constructed in the form of an open reading frame uninterrupted by internal-non-translated sequences, or introns, that are typically present in eukaryotic genes. Sequences of non-translated DNA can be present 5' or 3' from an open reading frame, where the same do not interfere with manipulation or expression of the coding region.

Nucleic acid molecules of the invention include DNA in both single-stranded and double-stranded form, as well as the RNA complement thereof. DNA includes, for example, cDNA, genomic DNA, chemically synthesized DNA, DNA amplified by PCR and combinations thereof. Genomic DNA may be isolated by conventional techniques, e.g., using the cDNA of SEQ ID NO:1 or SEQ ID NO:3, or a suitable fragment thereof, as a probe.

The DNA molecules of the invention include full length genes as well as polynucleotides and fragments thereof. The nucleic acids of the invention are derived from either murine or human sources, but the invention includes those derived from other sources as well.

Preferred Sequences

Particularly preferred nucleotide sequences of the invention are the murine sequence set forth in SEQ ID NO:1 and the human sequence set forth in SEQ ID NO:3. The sequences of amino acids encoded by the DNA of SEQ ID NO:1 and SEQ ID NO:3 are shown in SEQ ID NO:2 and SEQ ID NO:4, respectively. These sequences identify IL-1 delta polynucleotides as members of the IL-1 receptor family.

Additional Sequences

Due to the known degeneracy of the genetic code, wherein more than one codon can encode the same amino acid, a DNA sequence can vary from that shown in SEQ ID NO:1 or SEQ ID NO:3, and still encode a polypeptide having the amino acid sequence of SEQ ID NO:2 or SEQ ID NO:4. Such variant DNA sequences can result from silent mutations (e.g. occurring during PCR amplification), or can be the product of deliberate mutagenesis of a native sequence.

The invention thus provides isolated DNA sequences encoding polypeptides of the invention, selected from: (a) DNA comprising the nucleotide sequence of SEQ ID NO:1 or SEQ ID NO:3; (b) DNA encoding the polypeptides of SEQ ID NO:2 or SEQ ID NO:4; (c) DNA capable of hybridization to a DNA of (a) or (b) under conditions of moderate stringency and which encodes polypeptides of the invention; (d) DNA capable of hybridization to a DNA of (a) or (b) under conditions of high stringency and which encodes polypeptides of the invention, and (e) DNA which is degenerate as a result of the genetic code to a DNA defined in (a), (b), (c), or (d) and which encode polypeptides of the invention. Of course, polypeptides encoded by such DNA sequences are encompassed by the invention.

The invention thus provides equivalent isolated DNA sequences encoding biologically active IL-1 delta polypeptides selected from: (a) DNA derived from the coding region of a native mammalian IL-1 delta gene; (b) DNA selected from the group consisting of SEQ ID NO:1 or SEQ ID NO:3; (c) DNA capable of hybridization to a DNA of (a) or (b) under conditions of moderate stringency and which encodes biologically active IL-1 delta polypeptides; and (d) DNA that is degenerate as a result of the genetic code to a DNA defined in (a), (b) or (c), and which encodes biologically active IL-1 delta polypeptides. IL-1 delta polypeptides encoded by such DNA equivalent sequences are encompassed by the invention. IL-1 delta polypeptides encoded by DNA derived from other mammalian species, wherein the DNA will hybridize to the complement of the DNA of SEQ ID NO:1 or SEQ ID NO:3, are also encompassed.

As used herein, conditions of moderate stringency can be readily determined by those having ordinary skill in the art based on, for example, the length of the DNA. The basic conditions are set forth by Sambrook et al. *Molecular Cloning. A Laboratory Manual,* 2 ed. Vol. 1, pp. 1.101-104, Cold Spring Harbor Laboratory Press, (1989), and include use of a prewashing solution for the nitrocellulose filters 5×SSC, 0.5% SDS, 1.0 mM EDTA (pH 8.0), hybridization conditions of about 50% formamide, 6×SSC at about 42° C. (or other similar hybridization solution, such as Stark's solution, in about 50% formamide at about 42° C.), and washing conditions of about 60° C., 0.5×SSC, 0.1% SDS. Conditions of high stringency can also be readily determined by the skilled artisan based on, for example, the length of the DNA. Generally, such conditions are defined as hybridization conditions as above, and with washing at approximately 68° C., 0.2×SSC, 0.1% SDS. The skilled artisan will recognize that the temperature and wash solution salt concentration can be adjusted as necessary according to factors such as the length of the probe.

Also included as an embodiment of the invention is DNA encoding polypeptide fragments and polypeptides comprising inactivated N-glycosylation site(s), inactivated protease processing site(s), or conservative amino acid substitution(s), as described below.

In another embodiment, the nucleic acid molecules of the invention also comprise nucleotide sequences that are at least 80% identical to a native sequence. Also contemplated are embodiments in which a nucleic acid molecule comprises a sequence that is at least 90% identical, at least 95% identical, at least 98% identical, at least 99% identical, or at least 99.9% identical to a native sequence.

The percent identity may be determined by visual inspection and mathematical calculation. Alternatively, the percent identity of two nucleic acid sequences can be determined by comparing sequence information using the GAP computer program, version 6.0 described by Devereux et al. (*Nucl. Acids Res.* 12:387, 1984) and available from the Universiiy of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353-358, 1979; (2) a penalty of 3.0 for each gap and an additional 0.10 penalty for each symbol in each gap; and (3) no penalty for end gaps. Other programs used by one skilled in the art of sequence comparison may also be used.

The invention also provides isolated nucleic acids useful in the production of polypeptides. Such polypeptides may be prepared by any of a number of conventional techniques. A DNA sequence encoding a IL-1 delta polypeptide, or desired fragment thereof, may be subcloned into an expression vector for production of the polypeptide or fragment. The DNA sequence advantageously is fused to a sequence encoding a suitable leader or signal peptide. Alternatively, the desired fragment may be chemically synthesized using known techniques. DNA fragments also may be produced by restriction endonuclease digestion of a full length cloned DNA sequence, and isolated by electrophoresis on agarose gels. If necessary, oligonucleotides that reconstruct the 5' or 3' terminus to a desired point may be ligated to a DNA fragment generated by restriction enzyme digestion. Such oligonucleotides may additionally contain a restriction endonuclease cleavage site upstream of the desired coding sequence, and position an initiation codon (ATG) at the N-terminus of the coding sequence.

The well-known polymerase chain reaction (PCR) procedure also may be employed to isolate and amplify a DNA sequence encoding a desired protein fragment. Oligonucleotides that define the desired termini of the DNA fragment are employed as 5' and 3' primers. The oligonucleotides may additionally contain recognition sites for restriction endonucleases, to facilitate insertion of the amplified DNA fragment into an expression vector. PCR techniques are described in Saiki et al., *Science* 239:487 (1988); *Recombinant DNA Methodology*, Wu et al., eds., Academic Press, Inc., San Diego (1989), pp. 189-196; and *PCR Protocols: A Guide to Methods and Applications*, Innis et al., eds., Academic Press, Inc. (1990).

Polypeptides and Fragments Thereof

The invention encompasses polypeptides and fragments thereof in various forms, including those that are naturally occurring or produced through various techniques such as procedures involving recombinant DNA technology. For example, DNAs encoding IL-1 delta polypeptides can be derived from SEQ ID NO:1 or SEQ ID NO:3 by in vitro mutagenesis, which includes site-directed mutagenesis, random mutagenesis, and in vitro nucleic acid synthesis. Such forms include, but are not limited to, derivatives, variants, and oligomers, as well as fusion proteins or fragments thereof.

Polypeptides and Fragments Thereof

The polypeptides of the invention include full length proteins encoded by the nucleic acid sequences set forth above. Particularly preferred polypeptides comprise the amino acid sequence of SEQ ID NO:2 or SEQ ID NO:4.

The polypeptides of the invention may be membrane bound or they may be secreted and thus soluble. Soluble polypeptides are capable of being secreted from the cells in which they are expressed. In general, soluble polypeptides may be identified (and distinguished from non-soluble membrane-bound counterparts) by separating intact cells which express the desired polypeptide from the culture medium, e.g., by centrifugation, and assaying the medium (supernatant) for the presence of the desired polypeptide. The presence of polypeptide in the medium indicates that the polypeptide was secreted from the cells and thus is a soluble form of the protein.

In general, the use of soluble forms is advantageous for certain applications. Purification of the polypeptides from recombinant host cells is facilitated, since the soluble polypeptides are secreted from the cells. Further, soluble polypeptides are generally more suitable for intravenous administration.

The invention also provides polypeptides and fragments of the IL-1 delta that retain a desired biological activity. Particular embodiments are directed to polypeptide fragments that retain the ability to bind IL-1 delta counterstructures, such as IL-1 family members. Such a fragment may be a soluble polypeptide, as described above. In another embodiment, the polypeptides and fragments advantageously include regions that are conserved in the IL-1 delta family as described above.

Also provided herein are polypeptide fragments of varying lengths. In one embodiment, a preferred IL-1 delta polypeptide fragment comprises at least 6 contiguous amino acids of an amino acid sequence. In other embodiments, a preferred IL-1 delta polypeptide fragment comprises at least 10, at least 20, at least 30, up to at least 100 contiguous amino acids of the amino acid sequences of SEQ ID NO:2 and/or SEQ ID NO:4. These polypeptides can be produced in soluble form. In addition, fragments find use in studies of signal transduction, and in regulating cellular processes associated with transduction of biological signals. Polypeptide fragments also may be employed as immunogens, in generating antibodies.

Variants

Naturally occurring variants as well as derived variants of the polypeptides and fragments are provided herein.

An "IL-1 delta variant" as referred to herein means a polypeptide substantially homologous to native IL-1 delta polypeptide, but which has an amino acid sequence different from that of native IL-1 delta polypeptide (human, murine or other mammalian species) because of one or more deletions, insertions, or substitutions. The variant has an amino acid sequence that preferably is at least 80% identical to a native IL-1 delta polypeptide amino acid sequence, most preferably at least 90% identical. The percent identity may be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl Acids Res.* 14:6745, 1986, as described by Schwartz and Dayhoff, eds., *Atlas of Protein Sequence and Structure*, National Biomedical Research Foundation, pp. 353-358, 1979; (2) a penalty of 3.0 for each gap and an additional 0.10 penalty for each symbol in each gap; and (3) no penalty for end gaps.

Variants also include embodiments in which a polypeptide or fragment comprises an amino acid sequence that is at least 90% identical, at least 95% identical, at least 98% identical, at least 99% identical, or at least 99.9% identical to the preferred polypeptide or fragment thereof. Percent identity may be determined as above. Alternatively, the percent identity of two protein sequences can be determined by comparing sequence information using the GAP computer program, based on the algorithm of Needleman and Wunsch (J. Mol. Bio. 48:443, 1970) and available from the University of Wisconsin Genetics Computer Group (UWGCG). The preferred default parameters for the GAP program include: (1) a scoring matrix, blosum62, as described by Henikoff and Henikoff (Proc. Natl. Acad. Sci. USA 89:10915, 1992); (2) a gap weight of 12; (3) a gap length weight of 4; and (4) no penalty for end gaps. Other programs used by one skilled in the art of sequence comparison may also be used.

The variants of the invention include, for example, those that result from alternate mRNA splicing events or from proteolytic cleavage. Alternate splicing of mRNA may, for example, yield a truncated but biologically active protein, such as a naturally occurring soluble form of the protein. Variations attributable to proteolysis include, for example, differences in the N- or C-termini upon expression in different types of host cells, due to proteolytic removal of one or more terminal amino acids from the protein (generally from 1-5 terminal amino acids). Proteins in which differences in amino acid sequence are attributable to genetic polymorphism (allelic variation among individuals producing the protein) are also contemplated herein.

As stated above, the invention provides isolated and purified, or homogeneous, IL-1 delta polypeptides, both recombinant and non-recombinant. Variants and derivatives of native IL-1 delta proteins that retain the desired biological activity can be obtained by mutations of nucleotide sequences coding for native IL-1 delta polypeptides. Alterations of the native amino acid sequence can be accomplished by any of a number of conventional methods. Mutations can be introduced at particular loci by synthesizing oligonucleotides containing a mutant sequence flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene, wherein predetermined codons can be altered by substitution, deletion, or insertion. Exemplary methods of making the alterations set forth above are disclosed by Walder et al. (*Gene* 42:133, 1986); Bauer et al. (*Gene* 37:73, 1985); Craik (*BioTechniques*, January 1985, 12-19); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462, all of which are incorporated by reference.

IL-1 delta polypeptides can be modified to create IL-1 delta derivatives by forming covalent or aggregative conjugates with other chemical moieties, such as glycosyl groups, polyethylene glycol (PEG) groups, lipids, phosphate, acetyl groups and the like. Covalent derivatives of IL-1 delta polypeptides can be prepared by linking the chemical moieties to functional groups on IL-1 delta amino acid side chains or at the N-terminus or C-terminus of a IL-1 delta polypeptide or the extracellular domain thereof. Other derivatives of IL-1 delta polypeptides within the scope of this invention include covalent or aggregative conjugates of IL-1 delta polypeptides or their fragments with other proteins or polypeptides, such as by synthesis in recombinant culture as N-terminal or C-terminal fusions. For, example, the conjugate can comprise a signal or leader polypeptide sequence (e.g. the α-factor leader of *Saccharomyces*) at the N-terminus of a IL-1 delta polypeptide. The signal or leader peptide co-translationally or post-translationally directs transfer of the conjugate from its site of synthesis to a site inside or outside of the cell membrane or cell wall.

Conjugates comprising diagnostic (detectable) or therapeutic agents attached thereto are contemplated herein, as discussed in more detail below.

Other derivatives include covalent or aggregative conjugates of the polypeptides with other proteins or polypeptides, such as by synthesis in recombinant culture as N-terminal or C-terminal fusions. Examples of fusion proteins are discussed below in connection with oligomers. Further, fusion proteins can comprise peptides added to facilitate purification and identification. Such peptides include, for example, poly-His or the antigenic identification peptides described in U.S. Pat. No. 5,011,912 and in Hopp et al., *Bio/Technology* 6:1204, 1988. One such peptide is the FLAG® peptide, Asp-Tyr-Lys-Asp-Asp-Asp-Asp-Lys (SEQ ID NO:5), which is highly antigenic and provides an epitope reversibly bound by a specific monoclonal antibody, enabling rapid assay and facile purification of expressed recombinant protein. A murine hybridoma designated 4E11 produces a monoclonal antibody that binds the FLAG® peptide in the presence of certain divalent metal cations, as described in U.S. Pat. No. 5,011,912, hereby incorporated by reference. The 4E11 hybridoma cell line has been deposited with the American Type Culture Collection under accession no. HB 9259. Monoclonal antibodies that bind the FLAG® peptide are available from Eastman Kodak Co., Scientific Imaging Systems Division, New Haven, Conn.

Among the variant polypeptides provided herein are variants of native polypeptides that retain the native biological activity or the substantial equivalent thereof. One example is a variant that binds with essentially the same binding affinity as does the native form. Binding affinity can be measured by conventional procedures, e.g., as described in U.S. Pat. No. 5,512,457 and as set forth below.

Variants include polypeptides that are substantially homologous to the native form, but which have an amino acid sequence different from that of the native form because of one or more deletions, insertions or substitutions. Particular embodiments include, but are not limited to, polypeptides that comprise from one to ten deletions, insertions or substitutions of amino acid residues, when compared to a native sequence.

A given amino acid may be replaced, for example, by a residue having similar physiochemical characteristics. Examples of such conservative substitutions include substitution of one aliphatic residue for another, such as Ile, Val, Leu, or Ala for one another, substitutions of one polar residue for another, such as between Lys and Arg, Glu and Asp, or Gln and Asn; or substitutions of one aromatic residue for another, such as Phe, Trp, or Tyr for one another. Other conservative substitutions, e.g., involving substitutions of entire regions having similar hydrophobicity characteristics, are well known.

Similarly, the DNAs of the invention include variants that differ from a native DNA sequence because of one or more deletions, insertions or substitutions, but that encode a biologically active polypeptide.

The invention further includes polypeptides of the invention with or without associated native-pattern glycosylation. Polypeptides expressed in yeast or mammalian expression systems (e.g., COS-1 or COS-7 cells) can be similar to or significantly different from a native polypeptide in molecular weight and glycosylation pattern, depending upon the choice of expression system. Expression of polypeptides of the invention in bacterial expression systems, such as *E. coli*, provides non-glycosylated molecules. Further, a given preparation may include-multiple differentially glycosylated species of the protein. Glycosyl groups can be removed through conventional methods, in particular those utilizing glycopeptidase. In general, glycosylated polypeptides of the invention can be incubated with a molar excess of glycopeptidase (Boehringer Mannheim).

Correspondingly, similar DNA constructs that encode various additions or substitutions of amino acid residues or sequences, or deletions of terminal or internal residues or sequences are encompassed by the invention. For example, N-glycosylation sites in the polypeptide extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. Appropriate substitutions, additions, or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Alternatively, the Ser or Thr can by replaced with another amino acid, such as Ala. Known procedures for inactivating N-glycosylation sites in proteins include those described in U.S. Pat. No. 5,071,972 and EP 276,846, hereby incorporated by reference.

In another example of variants, sequences encoding Cys residues that are not essential for biological activity can be altered to cause the Cys residues to be deleted or replaced with other amino acids, preventing formation of incorrect intramolecular disulfide bridges upon folding or renaturation.

Other variants are prepared by modification of adjacent dibasic amino acid residues, to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites.

Oligomers

Encompassed by the invention are oligomers or fusion proteins that contain IL-1 delta polypeptides. Such oligomers may be in the form of covalently-linked or non-covalently-linked multimers, including dimers, trimers, or higher oligomers. As noted above, preferred polypeptides are soluble and thus these oligomers may comprise soluble polypeptides. In one aspect of the invention, the oligomers maintain the binding ability of the polypeptide components and provide therefor, bivalent, trivalent, etc., binding sites.

One embodiment of the invention is directed to oligomers comprising multiple polypeptides joined via covalent or non-covalent interactions between peptide moieties fused to the polypeptides. Such peptides may be peptide linkers (spacers), or peptides that have the property of promoting oligomerization. Leucine zippers and certain polypeptides derived from antibodies are among the peptides that can promote oligomerization of the polypeptides attached thereto, as described in more detail below.

Immunoglobulin-Based Oligomers

As one alternative, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al. (*PNAS USA* 88:10535, 1991); Byrn et al. (*Nature* 344:677, 1990); and Hollenbaugh and Aruffo ("Construction of Immunoglobulin Fusion Proteins", in *Current Protocols in Immunology*, Suppl. 4, pages 10.19.1-10.19.11, 1992).

One embodiment of the present invention is directed to a dimer comprising two fusion proteins created by fusing a polypeptide of the invention to an Fc polypeptide derived from an antibody. A gene fusion encoding the polypeptide/Fc fusion protein is inserted into an appropriate expression vector. Polypeptide/Fc fusion proteins are expressed in host cells transformed with the recombinant expression vector, and allowed to assemble much like antibody molecules, whereupon interchain disulfide bonds form between the Fc moieties to yield divalent molecules.

The term "Fc polypeptide" as used herein includes native and mutein forms of polypeptides made up of the Fc region of an antibody comprising any or all of the CH domains of the Fc region. Truncated forms of such polypeptides containing the hinge region that promotes dimerization are also included. Preferred polypeptides comprise an Fc polypeptide derived from a human IgG1 antibody.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., (*EMBO J.* 13:3992-4001, 1994) incorporated herein by reference. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

The above-described fusion proteins comprising Fc moieties (and oligomers formed therefrom) offer the advantage of facile purification by affinity chromatography over Protein A or Protein G columns.

In other embodiments, the polypeptides of the invention may be substituted for the variable portion of an antibody heavy or light chain. If fusion proteins are made with both heavy and light chains of an antibody, it is possible to form an oligomer with as many as four IL-1 delta extracellular regions.

Peptide-Linker Based Oligomers

Alternatively, the oligomer is a fusion protein comprising multiple polypeptides, with or without peptide linkers (spacer peptides). Among the suitable peptide linkers are those described in U.S. Pat. Nos. 4,751,180 and 4,935,233, Which are hereby incorporated by reference. A DNA sequence encoding a desired peptide linker may be inserted between, and in the same reading frame as, the DNA sequences of the invention, using any suitable conventional technique. For example, a chemically synthesized oligonucleotide encoding the linker may be ligated between the sequences. In particular embodiments, a fusion protein comprises from two to four soluble IL-1 delta polypeptides, separated by peptide linkers.

Leucine-Zippers

Another method for preparing the oligomers of the invention involves use of a leucine zipper. Leucine zipper domains are peptides that promote oligomerization of the proteins in which they are found. Leucine zippers were originally identified in several DNA-binding proteins (Landschulz et al., *Science* 240:1759, 1988), and have since been found in a variety of different proteins. Among the known leucine zippers are naturally occurring peptides and derivatives thereof that dimerize or trimerize.

The zipper domain (also referred to herein as an oligomerizing, or oligomer-forming, domain) comprises a repetitive heptad repeat, often with four or five leucine residues interspersed with other amino acids. Examples of zipper domains are those found in the yeast transcription factor GCN4 and a heat-stable DNA-binding protein found in rat liver (C/EBP; Landschulz et al., *Science* 243:1681, 1989). Two nuclear transforming proteins, fos and jun, also exhibit zipper domains, as does the gene product of the murine proto-oncogene, c-myc (Landschulz et al., *Science* 240:1759, 1988). The products of the nuclear oncogenes fos and jun comprise zipper domains that preferentially form heterodimer (O'Shea et al., *Science* 245:646, 1989, Turner and Tjian, *Science* 243:1689, 1989). The zipper domain is necessary for biological activity (DNA binding) in these proteins.

The fusogenic proteins of several different viruses, including paramyxovirus, coronavirus, measles virus and many retroviruses, also possess zipper domains (Buckland and Wild, *Nature* 338:547, 1989; Britton, *Nature* 353:394, 1991; Delwart and Mosialos, *AIDS Research and Human Retroviruses* 6:703, 1990). The zipper domains in these fusogenic viral proteins are near the transmembrane region of the proteins; it has been suggested that the zipper domains could contribute to the oligomeric structure of the fusogenic proteins. Oligomerization of fusogenic viral proteins is involved in fusion pore formation (Spruce et al, *Proc. Natl. Acad. Sci. U.S.A.* 88:3523, 1991). Zipper domains have also been recently reported to play a role in oligomerization of heat-shock transcription factors (Rabindran et al., *Science* 259:230, 1993).

Zipper domains fold as short, parallel coiled coils (O'Shea et al., *Science* 254:539; 1991). The general architecture of the parallel coiled coil has been well characterized, with a "knobs-into-holes" packing as proposed by Crick in 1953 (*Acta Crystallogr.* 6:689). The dimer formed by a zipper domain is stabilized by the heptad repeat, designated $(abcdefg)_n$ according to the notation of McLachlan and Stewart (*J. Mol. Biol.* 98:293; 1975), in which residues a and d are generally hydrophobic residues, with d being a leucine, which line up on the same face of a helix. Oppositely-charged residues commonly occur at positions g and e. Thus, in a parallel coiled coil formed from two helical zipper domains, the "knobs" formed by: the hydrophobic side chains of the first helix are packed into the "holes" formed between the side chains of the second helix.

The residues at position d (often leucine) contribute large hydrophobic stabilization energies, and are important for oligomer formation (Krystek: et al., *Int. J. Peptide Res.* 38:229, 1991). Lovejoy et al. (*Science* 259:1288, 1993) recently reported the synthesis of a triple-stranded α-helical bundle in which the helices run up-up-down. Their studies confirmed that hydrophobic stabilization energy provides the main driving force for the formation of coiled coils from helical monomers. These studies also indicate that electrostatic interactions contribute to the stoichiometry and geometry of coiled coils. Further discussion of the structure of leucine zippers is found in Harbury et al. (*Science* 262:1401, 26 Nov. 1993).

Examples of leucine zipper domains suitable for producing soluble oligomeric proteins are described in PCT application WO 94/10308, and the leucine zipper derived from lung surfactant protein D (SPD) described in Hoppe et al. (*FEBS Letters* 344:191, 1994), hereby incorporated by reference. The use of a modified leucine zipper that allows for stable trimerization of a heterologous protein fused thereto is described in Fanslow et al. (*Semin. Immunol.* 6:267-278, 1994). Recombinant fusion proteins comprising a soluble polypeptide fused to a leucine zipper peptide are expressed in suitable host cells, and the soluble oligomer that forms is recovered from the culture supernatant.

Certain leucine zipper moieties preferentially form trimers. One example is a leucine zipper derived from lung surfactant protein D (SPD), as described in Hoppe et al. (*FEBS Letters* 344:191, 1994) and in U.S. Pat. No. 5,716, 805, hereby incorporated by reference in their entirety. This lung SPD-derived leucine zipper peptide comprises the amino acid sequence Pro Asp Val Ala Ser Leu Arg Gln Gln Val Glu Ala Leu Gln Gly Gln Val Gln His Leu Gln Ala Ala Phe Ser Gln Tyr (SEQ ID NO:6).

Another example of a leucine zipper that promotes trimerization is a peptide comprising the amino acid sequence Arg Met Lys Gln Ile Glu Asp Lys Ile Glu Glu Ile Leu Ser Lys Ile Tyr His Ile Glu Asn Glu Ile Ala Arg Ile Lys Lys Leu Ile Gly Glu Arg (SEQ ID NO:7), as described in U.S. Pat. No. 5,716,805. In one alternative embodiment, an N-terminal Asp residue is added; in another, the peptide lacks the N-terminal Arg residue.

Fragments of the foregoing zipper peptides that retain the property of promoting oligomerization may be employed as well. Examples of such fragments include, but are not limited to, peptides lacking one or two of the N-terminal or C-terminal residues presented in the foregoing amino acid sequences. Leucine zippers may be derived from naturally occurring leucine zipper peptides, e.g., via conservative substitution(s) in the native amino acid sequence, wherein the peptide's ability to promote oligomerization is retained.

Other peptides derived from naturally occurring trimeric proteins may be employed in preparing trimeric IL-1 delta. Alternatively, synthetic peptides that promote oligomerization may be employed. In particular embodiments, leucine residues in a leucine zipper moiety are replaced by isoleucine residues. Such peptides comprising isoleucine may be referred to as isoleucine zippers, but are encompassed by the term "leucine zippers" as employed herein.

Production of Polypeptides and Fragments Thereof

Expression, isolation and purification of the polypeptides and fragments of the invention may be accomplished by any suitable technique, including but not limited to the following:

Expression Systems

The present invention also provides recombinant cloning and expression vectors containing DNA, as well as host cell containing the recombinant vectors. Expression vectors comprising DNA may be used to prepare the polypeptides or fragments of the invention encoded by the DNA. A method for producing polypeptides comprises culturing host cells transformed with a recombinant expression vector encoding the polypeptide, under conditions that promote expression of the polypeptide, then recovering the expressed polypeptides from the culture. The skilled artisan will recognize that the procedure for purifying the expressed polypeptides will vary according to such factors as the type of host cells employed, and whether the polypeptide is membrane-bound or a soluble form that is secreted from the host cell.

Any suitable expression system may be employed. The vectors include a DNA encoding a polypeptide or fragment of the invention, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide upon secretion of polypeptide from the cell.

Suitable host cells for expression of polypeptides include prokaryotes, yeast or higher eukaryotic cells. Mammalian or insect cells are generally preferred for use as host cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce polypeptides using RNAs derived from DNA constructs disclosed herein.

Prokaryotic Systems

Prokaryotes include gram-negative or gram-positive organisms. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, a polypeptide may include an N-terminal methionine residue to facilitate expression of the recombinant polypeptide in the prokaryotic host cell. The N-terminal Met may be cleaved from the expressed recombinant polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage $\lambda P_L$ promoter and a cI857ts thermolabile repressor sequence. Plasmid vectors available from the American Type Culture Collection which incorporate derivatives of the $\lambda P_L$ promoter include plasmid pHUB2 (resident in *E. coli* strain JMB9, ATCC 37092) and pPLc28 (resident in *E. coli* RR1, ATCC 53082).

IL-1 delta DNA may be cloned in-frame into the multiple cloning site of an ordinary bacterial expression vector. Ideally the vector would contain an inducible promoter upstream of the cloning site, such that addition of an inducer leads to high-level production of the recombinant protein at a time of the investigator's choosing. For some proteins, expression levels may be boosted by incorporation of codons encoding a fusion partner (such as hexahistidine) between the promoter and the gene of interest. The resulting "expression plasmid" may be propagated in a variety of strains of *E. coli*.

For expression of the recombinant protein, the bacterial cells are propagated in growth medium until reaching a pre-determined optical density. Expression of the recombinant protein is then induced, e.g. by addition of IPTG (isopropyl-b-D-thiogalactopyranoside), which activates expression of proteins from plasmids containing a lac operator/promoter. After induction (typically for 14 hours), the cells are harvested by pelleting in a centrifuge, e.g. at 5,000×G for 20 minutes at 4° C.

For recovery of the expressed protein, the pelleted cells may be resuspended in ten volumes of 50 mM Tris-HCl (pH 8)/1 M NaCl and then passed two or three times through a French press. Most highly expressed recombinant proteins form insoluble aggregates known as inclusion bodies. Inclusion bodies can be purified away from the soluble proteins by pelleting in a centrifuge at 5,000×G for 20 minutes, 4° C. The inclusion body pellet is washed with 50 mM Tris-HCl (pH 8)/1% Triton X-100 and then dissolved in 50 mM Tris-HCl (pH. 8)/8 M urea/0.1 M DTTf. Any material that cannot be dissolved is removed by centrifugation (10,000×G for 20 minutes, 20° C.). The protein of interest will, in most cases, be the most abundant protein in the resulting clarified supernatant. This protein may be "refolded" into the active conformation by dialysis against 50 mM Tris-HCl (pH 8)/5 mM $CaCl_2$/5 mM Zn(OAc)/1 mM GSSG/0.1 mM GSH. After refolding, purification can be carried out by a variety of chromatographic methods, such as ion exchange or gel filtration. In some protocols, initial purification may be carried out before refolding. As an example, hexahistidine-tagged fusion proteins may be partially purified on immobilized Nickel.

While the preceding purification and refolding procedure assumes that the protein is best recovered from inclusion bodies, those skilled in the art of protein purification will appreciate that many recombinant proteins are best purified out of the soluble fraction of cell lysates. In these cases, refolding is often not required, and purification by standard chromatographic methods can be carried out directly.

Yeast Systems

Alternatively, the polypeptides may be expressed in yeast host cells, preferably from the *Saccharomyces* genus (e.g., *S. cerevisiae*). Other genera of yeast, such as *Pichia* or *Kluyveromyces*, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceradehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase. Other suitable vectors and promoters for use in yeast expression are further described in Hitzeman, EPA-73,657. Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of the polypeptide. The α-factor leader sequence is often inserted between the promoter sequence and the structural gene sequence. See, e.g., Kurjan et al., *Cell* 30:933, 1982 and Bitter et al., *Proc. Natl. Acad. Sci. USA* 81:5330, 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 mg/ml adenine and 20 mg/ml uracil.

Yeast host cells transformed by vectors containing an ADH2 promoter sequence may be grown for inducing expression in a "rich" medium. An example of a rich medium is one consisting of 1% yeast extract, 2% peptone, and 1% glucose supplemented with 80 mg/ml adenine and 80 mg/ml uracil. Derepression of the ADH2 promoter occurs when glucose is exhausted from the medium.

Mammalian or Insect Systems

No Mammalian or insect host cell culture systems also may be employed to express recombinant polypeptides. Bacculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by McMahan et al. (*EMBO J.* 10: 2821, 1991).

Established methods for introducing DNA into mammalian cells have been described (Kaufman, R. J., *Large Scale Mammalian Cell Culture*, 1990, pp. 15-69). Additional protocols using commercially available reagents, such as Lipofectamine lipid reagent (Gibco/BRL) or Lipofectamine-Plus lipid reagent, can be used to transfect cells (Felgner et al., *Proc. Natl. Acad. Sci. USA* 84:7413-7417, 1987). In addition, electroporation can be used to transfect mammalian cells using conventional procedures, such as those in Sambrook et al. (*Molecular Cloning: A Laboratory Manual*, 2 ed. Vol. 1-3, Cold Spring Harbor Laboratory Press, 1989). Selection of stable transformants can be performed using methods known in the art, such as, for example, resistance to cytotoxic drugs. Kaufman et al., *Meth. in Enzymology* 185:487-511, 1990, describes several selection schemes, such as dihydrofolate reductase (DHFR) resistance. A suitable host strain for DHFR selection can be CHO strain DX-B11, which is deficient in DHFR (Urlaub and Chasin, *Proc. Natl. Acad. Sci. USA* 77:4216-4220, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., *Nature* 273:113, 1978; Kaufman, *Meth. in Enzymology*, 1990). Smaller or larger SV40 fragments can also be used, provided the approximately 250 bp sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., *Animal Cell Technology*, 1997, pp. 529-534 and PCT Application WO 97/25420) and the tripartite leader (TPL) and VA gene RNAs from Adenovirus 2 (Gingeras et al., *J. Biol. Chem.* 257:13475-13491, 1982). The internal ribosome entry site (IRES) sequences of viral origin allows dicistronic mRNAs to be translated efficiently (Oh and Sarnow, *Current Opinion in Genetics and Development* 3:295-300, 1993; Ramesh et al., *Nucleic Acids Research* 24:2697-2700, 1996). Expression of a heterologous cDNA as part of a dicistronic mRNA followed by the gene for a selectable marker (e.g. DHFR) has been shown to improve transfectability of the host and expression of the heterologous cDNA (Kaufman, *Meth. in Enzymology*, 1990). Exemplary expression vectors that employ dicistronic mRNAs are pTR-DC/GFP described by Mosser et al., *Biotechniques* 22:150-161, 1997, and p2A5I described by Morris et al., *Animal Cell Technology*, 1997, pp. 529-534.

A useful high expression vector, pCAVNOT, has been described by Mosley et al., *Cell* 59:335-348, 1989. Other expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984, has been deposited as ATCC 39890. Additional useful mammalian expression vectors are described in EP-A-0367566, and in WO 91/18982, incorporated by reference herein. In yet another alternative, the vectors can be derived from retroviruses.

Additional useful expression vectors, pFLAG® and pDC311, can also be used. FLAG® technology is centered on the fusion of a low molecular weight (1 kD), hydrophilic, FLAGS marker peptide to the N-terminus of a recombinant protein expressed by pFLAG® expression vectors. pDC311 is another specialized vector used for expressing proteins in CHO cells. pDC311 is characterized by a bicistronic sequence containing the gene of interest and a dihydrofolate reductase (DHFR) gene with an internal ribosome binding site for DHFR translation, an expression augmenting sequence element (EASE), the human CMV promoter, a tripartite leader sequence, and a polyadenylation site.

Regarding signal peptides that may be employed, a heterologous signal peptide or leader sequence may be used, if desired. The choice of signal peptide or leader may depend on factors such as the type of host cells in which the recombinant polypeptide is to be produced. To illustrate, examples of heterologous signal peptides that are functional in mammalian host cells include the signal sequence for interleukin-7 (IL-7) described in U.S. Pat. No. 4,965,195; the signal sequence for interleukin-2 receptor described in Cosman et al., *Nature* 312:768 (1984); the interleukin-4 receptor signal peptide described in EP 367,566; the type I interleukin-1 receptor signal peptide described in U.S. Pat. No. 4,968,607; and the type II interleukin-1 receptor signal peptide described in EP 460,846.

Purification

The invention also includes methods of isolating and purifying the polypeptides and fragments thereof. An isolated and purified IL-1 delta polypeptide according to the invention can be produced by recombinant expression systems as described above or purified from naturally occurring cells. IL-1 delta polypeptide can be substantially purified, as indicated by a single protein band upon analysis by SDS-polyacrylamide gel electrophoresis (SDS-PAGE). One process for producing IL-1 delta comprises culturing a host cell transformed with an expression vector comprising a DNA sequence that encodes IL-1 delta polypeptide under conditions sufficient to promote expression of IL-1 delta. IL-1 delta polypeptide is then recovered from culture medium or cell extracts, depending upon the expression system employed.

Isolation and Purification

The expression "isolated and purified" as used herein means that IL-1 delta is essentially free of association with other DNA, proteins, or polypeptides, for example, as a purification product of recombinant host cell culture or as a purified product from a non-recombinant source. The term "substantially purified" as used herein refers to a mixture that contains IL-1 delta and is essentially free of association with other DNA, proteins, or polypeptides, but for the presence of known DNA or proteins that can be removed using a specific antibody, and which substantially purified IL-1 delta proteins retain biological activity. The term "purified IL-1 delta" refers to either the "isolated and purified" form of IL-1 delta or the "substantially purified" form of IL-1 delta, as both are described herein.

The term "biologically active" as it refers to IL-1 delta protein, means that the IL-1 delta protein is capable of associating with IL-1 delta counterstructures or being co-immunoprecipitated with IL-1 delta counterstructures using an antibody to the IL-1 delta counterstructure.

In one preferred embodiment, the purification of recombinant polypeptides or fragments can be accomplished using fusions of polypeptides or fragments of the invention to another polypeptide to aid in the purification of polypeptides or fragments of the invention. Such fusion partners can include the poly-His or other antigenic identification peptides described above as well as the Fc moieties described previously.

With respect to any type of host cell, as is known to the skilled artisan, procedures for purifying a recombinant polypeptide or fragment will vary according to such factors as the type of host cells employed and whether or not the recombinant polypeptide or fragment is secreted into the culture medium.

In general, the recombinant polypeptide or fragment can be isolated from the host cells if not secreted, or from the medium or supernatant if soluble and secreted, followed by one or more concentration, salting-out, ion exchange, hydrophobic interaction, affinity purification or size exclusion chromatography steps. As to specific ways to accomplish these steps, the culture medium first can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. In addition, a chromatofocusing step can be employed. Alternatively, a hydrophobic interaction chromatography step can be employed. Suitable matrices can be phenyl or octyl moieties bound to resins. In addition, affinity chromatography with a matrix which selectively binds the recombinant protein can be employed. Examples of such resins employed are lectin columns, dye columns, and metal-chelating columns. Finally, one or more reversed-phase high performance liquid chromatography (RP-HPLC) steps employing hydrophobic RP-HPLC media, (e.g., silica gel or polymer resin having pendant methyl, octyl, octyldecyl or other aliphatic groups) can be employed to further purify the polypeptides. Some or all of the foregoing purification steps, in various combinations, are well known and can be employed to provide an isolated and purified recombinant protein.

Recombinant protein produced in bacterial culture is usually isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells are preferably employed to express IL-1 delta as a secreted polypeptide in order to simplify purification. Secreted recombinant polypeptide from a yeast host cell fermentation can be purified by methods analogous to those disclosed by Urdal et al. (*J. Chromatog.* 296:171, 1984). Urdal et al. describe two sequential, reversed-phase HPLC steps for purification of recombinant human IL-2 on a preparative HPLC column.

It is also possible to utilize an affinity column comprising a polypeptide-binding protein of the invention, such as a monoclonal antibody generated against polypeptides of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention.

In this aspect of the invention, polypeptide-binding proteins, such as the anti-polypeptide antibodies of the invention or other proteins that may interact with the polypeptide of the invention, can be bound to a solid phase support such as a column chromatography matrix or a similar substrate suitable for identifying, separating, or purifying cells that express polypeptides of the invention on their surface. Adherence of polypeptide-binding proteins of the invention to a solid phase contacting surface can be accomplished by any means, for example, magnetic microspheres can be coated with these polypeptide-binding proteins and held in the incubation vessel through a magnetic field. Suspensions of cell mixtures are contacted with the solid phase that has such polypeptide-binding proteins thereon. Cells having polypeptides of the invention on their surface bind to the fixed polypeptide-binding protein and unbound cells then are washed away. This affinity-binding method is useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner.

Alternatively, mixtures of cells suspected of containing polypeptide-expressing cells of the invention first can be incubated with a biotinylated polypeptide-binding protein of the invention. Incubation periods are typically at least one hour in duration to ensure sufficient binding to polypeptides of the invention. The resulting mixture then is passed through a column packed with avidin-coated beads, whereby the high affinity of biotin for avidin provides the binding of the polypeptide-binding cells to the beads. Use of avidin-coated beads is known in the art. See Berenson, et al. *J. Cell. Biochem.*, 10D:239 (1986). Wash of unbound material and the release of the bound cells is performed using conventional methods.

In the methods described above, suitable IL-1 delta-binding polypeptides are anti-IL-1 delta antibodies and other proteins that are capable of high-affinity binding of IL-1 delta. A preferred IL-1 delta-binding protein is an anti-IL-1 delta monoclonal antibody.

The desired degree of purity depends on the intended use of the protein. A relatively high degree of purity is desired when the polypeptide is to be administered in vivo, for example. In such a case, the polypeptides are purified such that no protein bands corresponding to other proteins are detectable upon analysis by SDS-polyacrylamide gel electrophoresis (SDS-PAGE). It will be recognized by one skilled in the pertinent field that multiple bands corresponding to the polypeptide may be visualized by SDS-PAGE, due to differential glycosylation, differential post-translational processing, and the like. Most preferably, the polypeptide of the invention is purified to substantial homogeneity, as indicated by a single protein band upon analysis by SDS-PAGE. The protein band may be visualized by silver staining, Coomassie blue staining, or (if the protein is radiolabeled) by autoradiography.

Assays

The purified polypeptides of the invention (including proteins, polypeptides, fragments, variants, oligomers, and other forms) may be tested for the ability to bind a IL-1 delta counter-structure molecule in any suitable assay, such as a conventional binding assay. To illustrate, the polypeptide may be labeled with a detectable reagent (e.g., a radionuclide, chromophore, enzyme that catalyzes a colorimetric or fluorometric reaction, and the like). The labeled polypeptide is contacted with cells expressing a IL-1 delta counter-structure molecule. The cells then are washed to remove unbound labeled polypeptide, and the presence of cell-bound label is determined by a suitable technique, chosen according to the nature of the label.

One example of a binding assay procedure is as follows. A recombinant expression vector containing a IL-1 delta counter-structure molecule cDNA is constructed, for example, fusing the extracellular domain of a IL-1 delta counter-structure molecule to the IgG-1 Fc (mutein form) as previously described for OX40-Fc (Baum et al., *EMBO J.* 13:3992-4001, 1994). CV1-EBNA-1 cells in 10 cm$^2$ dishes are transfected with the recombinant expression vector. CV-1/EBNA-1 cells (ATCC CRL 10478) constitutively express EBV nuclear antigen-1 driven from the CMV immediate-early enhancer/promoter. CV1-EBNA-1 was derived from the African Green Monkey kidney cell line CV-1 (ATCC CCL 70), as described by McMahan et al. (*EMBO J.* 10:2821, 1991).

The transfected cells are cultured for 24 hours, and the cells in each dish then are split into a 24-well plate. After culturing an additional 48 hours, the transfected cells (about 4×10$^4$ cells/well) are washed with BM-NFDM, which is binding medium (RPMI 1640 containing 25 mg/ml bovine serum albumin, 2 mg/ml sodium azide, 20 mM Hepes pH 7.2) to which 50 mg/ml nonfat dry milk has been added. The cells then are incubated for 1 hour at 37° C. with various concentrations of, for example, a soluble polypeptide/Fc fusion protein made as set forth above. Cells then are washed and incubated with a constant saturating concentration of a $^{125}$I-mouse anti-human IgG in binding medium, with gentle agitation for 1 hour at 37° C. After extensive washing, cells are released via trypsinization.

The mouse anti-human IgG employed above is directed against the Fc region of human IgG and can be obtained from Jackson Immunoresearch Laboratories, Inc., West Grove, Pa. The antibody is radioiodinated using the standard chloramine-T method. The antibody will bind to the Fc portion of any polypeptide/Fc protein that has bound to the cells. In all assays, non-specific binding of $^{125}$I-antibody is assayed in the absence of the Fc fusion protein, as well as in the presence of the Fc fusion protein and a 200-fold molar excess of unlabeled mouse anti-human IgG antibody.

Cell-bound $^{125}$I-antibody is quantified on a Packard Auto-gamma counter. Affinity calculations (Scatchard, *Ann. N.Y. Acad. Sci.* 51:660, 1949) are generated on RS/1 (BBN Software, Boston, Mass.) run on a Microvax computer.

Another type of suitable binding assay is a competitive binding assay. To illustrate, biological activity of a variant may be determined by assaying for the variants ability to compete with the native protein for binding to IL-1 delta counterstructures or cells expressing a IL-1 delta counter-structure.

Competitive binding assays can be performed by conventional methodology. Reagents that may be employed in competitive binding assays include radiolabeled IL-1 delta and intact cells expressing IL-1 delta counterstructures (endogenous or recombinant) on the cell surface. For example, a radiolabeled soluble IL-1 delta fragment can be used to compete with a soluble IL-1 delta variant for binding to cell surface (binding partner). Instead of intact cells, one could substitute a soluble IL-1 delta counterstructure/Fc fusion protein bound to a solid phase through the interaction of Protein A or Protein G (on the solid phase) with the Fc moiety. Chromatography columns that contain Protein A and Protein G include those available from Pharmacia Biotech, Inc., Piscataway, N.J.

Another type of competitive binding assay utilizes radiolabeled soluble IL-1 delta counterstructure such as a soluble IL-1 delta counterstructure/Fc fusion protein, and intact cells expressing IL-1 delta. Qualitative results can be obtained by competitive autoradiographic plate binding assays, while Scatchard plots (Scatchard, *Ann. N.Y. Acad. Sci.* 51:660, 1949) may be utilized to generate quantitative results.

Use of IL-1 Delta Nucleic Acid or Oligonucleotides

In addition to being used to express polypeptides as described above, the nucleic acid of the invention, including DNA, and oligonucleotides thereof can be used:
- as probes to identify nucleic acid encoding proteins having IL-1 delta activity;
- to identify human chromosome 2;
- to map genes on human chromosome 2;
- to identify genes associated with certain diseases, syndromes, or other conditions associated with human chromosome 2;
- as single-stranded sense or antisense oligonucleotides, to inhibit expression of polypeptide encoded by the IL-1 delta gene;
- to help detect defective genes in an individual; and
- for gene therapy.

Probes

Among the uses of nucleic acids of the invention is the use of fragments as probes or primers. Such fragments generally comprise at least about 17 contiguous nucleotides of a DNA sequence. In other embodiments, a DNA fragment comprises at least 30, or at least 60, contiguous nucleotides of a DNA sequence.

Because homologs of SEQ ID NO:1 and SEQ ID NO:3 from other mammalian species are contemplated herein, probes based on the DNA sequence of SEQ ID NO:1 or SEQ ID NO:3 may be used to screen cDNA libraries derived from other mammalian species, using conventional cross-species hybridization techniques.

Using knowledge of the genetic code in combination with the amino acid sequences set forth above, sets of degenerate oligonucleotides can be prepared. Such oligonucleotides are useful as primers, e.g., in polymerase chain reactions (PCR), whereby DNA fragments are isolated and amplified.

Due to the RNA expression pattern of IL-1 delta, probes based on the DNA sequence of SEQ ID NO:3 can be used to detect lymph node, thymus, tonsil, brain placenta, lung, skeletal muscle, prostate, and testis tissue and cell types by methods such as in situ hybridization.

Chromosome Mapping

Human IL-1 delta gene maps to chromosome 2q11-12. All or a portion of the nucleic acids of SEQ ID NO:3, including oligonucleotides, can be used by those skilled in the art using well-known techniques to identify human chromosome 2, and the specific locus thereof, that contains the DNA of IL-1 delta family members. Useful techniques include, but are not limited to, using the sequence or portions, including oligonucleotides, as a probe in various well-known techniques such as radiation hybrid mapping (high resolution), in situ hybridization to chromosome spreads (moderate resolution), and Southern blot hybridization to hybrid cell lines containing individual human chromosomes (low resolution).

For example, chromosomes can be mapped by radiation hybridization. PCR is performed using the Whitehead Institute/MIT Center for Genome Research Genebridge4 panel of 93 radiation hybrids (http://www-genome.wi.mit.edu/ftp/distribution/human STS releases/july97/rhmap/genebridge4.html). Primers are used which lie within a putative exon of the gene of interest and which amplify a product from human genomic DNA, but do not amplify hamster genomic DNA. The results of the PCRs are converted into a data vector that is submitted to the Whitehead/MIT Radiation Mapping site on the internet (http://www-seq.wi.mit.edu). The data is scored and the chromosomal assignment and placement relative to known Sequence Tag Site (STS) markers on the radiation hybrid map is provided. The following web site provides additional information about radiation hybrid mapping: http://www-genome.wi.mit.edu/ftp/distribution/human STS releases/july97/07-97.INTRO.html).

Identifying Associated Diseases

As set forth above, SEQ ID NO:3 has been mapped to the 2q11-12 region of chromosome 2. Human chromosome 2 is associated with specific diseases which include but are not limited to glaucoma, ectodermal dysplasia, insulin-dependent diabetes mellitus, wrinkly skin syndrome, T-cell leukemia/lymphoma, and tibial muscular dystrophy. Thus, the nucleic acid of SEQ ID NO:3, or a fragment thereof, can be used by one skilled in the art using well-known techniques to analyze abnormalities associated with gene mapping to chromosome 2. This enables one to distinguish conditions in which this marker is rearranged or deleted. In addition, nucleotides of SEQ ID NO:3 or a fragment thereof can be used as a positional marker to map other genes of unknown location.

The DNA may be used in developing treatments for any disorder mediated (directly or indirectly) by defective, or insufficient amounts of, the genes corresponding to the nucleic acids of the invention. Disclosure herein of native nucleotide sequences permits the detection of defective genes, and the replacement thereof with normal genes. Defective genes may be detected in in vitro diagnostic assays, and by comparison of a native nucleotide sequence disclosed herein with that of a gene derived from a person suspected of harboring a defect in this gene.

Sense-Antisense

Other useful fragments of the nucleic acids include antisense or sense oligonucleotides comprising a single-stranded nucleic acid sequence (either RNA or DNA) capable of binding to target mRNA (sense) or DNA (antisense) sequences. Antisense or sense oligonucleotides, according to the present invention, comprise a fragment of DNA (SEQ ID NO:1 or SEQ ID NO:3). Such a fragment generally comprises at least about 14 nucleotides, preferably from about 14 to about 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block or inhibit protein expression by one of several means, including enhanced degradation of the mRNA by RNAseH, inhibition of splicing, premature termination of transcription or translation, or by other means. The antisense oligonucleotides thus may be used to block expression of proteins. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, lipofection, CaPO$_4$-mediated DNA transfection, electroporation, or by using gene transfer vectors such as Epstein-Barr virus.

Sense or antisense oligonucleotides are preferably introduced into a cell containing the target nucleic acid sequence by insertion of the sense or antisense oligonucleotide into a suitable retroviral vector, then contacting the cell with the retrovirus vector containing the inserted sequence, either in vivo or ex vivo. Suitable retroviral vectors include, but are not limited to, the murine retrovirus M-MuLV, N2 (a retrovirus derived from M-MuLV), or the double copy vectors designated DCT5A, DCT5B and DCT5C (see PCT Application US 90/02656).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase. to a monoclonal antibody targeted to a specific cell type.

Use of IL-1 Delta Polypeptides and Fragmented Polypeptides

Uses include, but are not limited to, the following:
Purifying proteins and measuring activity thereof
Delivery Agents
Therapeutic Agents
Rational Drug Design
Research Reagents
Molecular weight and Isoelectric focusing markers
Controls for peptide fragmentation
Identification of unknown proteins
Preparation of Antibodies Purification Reagents Each of the polypeptides of the invention finds use as a protein purification reagent. The polypeptides may be attached to a solid support material and used to purify IL-1 delta counter-structure molecules by affinity chromatography. In particular embodiments, a polypeptide (in any form described herein that is capable of binding IL-1 delta counter-structure molecules) is attached to a solid support by conventional procedures. As one example, chromatography columns containing functional groups that will react with functional groups on amino acid side chains of proteins are available (Pharmacia Biotech, Inc., Piscataway, N.J.). In an alternative, a polypeptide/Fc protein (as discussed above) is attached to Protein A- or Protein G-containing chromatography columns through interaction with the Fc moiety.

The polypeptide also finds use in purifying or identifying cells that express IL-1 delta counter-structure molecules on the cell surface. Polypeptides are bound to a solid phase such as a column chromatography matrix or a similar suitable substrate. For example, magnetic microspheres can be coated with the polypeptides and held in an incubation vessel through a magnetic field. Suspensions of cell mixtures containing IL-1 delta counter-structure molecule-expressing cells are contacted with the solid phase having the polypeptides thereon. Cells expressing IL-1 delta counter-structure molecules on the cell surface bind to the fixed polypeptides, and unbound cells then are washed away.

Alternatively, the polypeptides can be conjugated to a detectable moiety, then incubated with cells to be tested for IL-1 delta counter-structure molecules expression. After incubation, unbound labeled matter is removed and the presence or absence of the detectable moiety on the cells is determined.

In a further alternative, mixtures of cells suspected of containing cells expressing IL-1 delta counter-structure molecules are incubated with biotinylated polypeptides. Incubation periods are typically at least one hour in duration to ensure sufficient binding. The resulting mixture then is passed through a column packed with avidin-coated beads, whereby the high affinity of biotin for avidin provides binding of the desired cells to the beads. Procedures for using avidin-coated beads are known (see Berenson, et al. *J. Cell. Biochem.*, 10D:239, 1986). Washing to remove unbound material, and the release of the bound cells, are performed using conventional methods.

Measuring Activity

Polypeptides also find use in measuring the biological activity of IL-1 delta counter-structure molecules in terms of their binding affinity. The polypeptides thus may be employed by those conducting "quality assurance" studies, e.g., to monitor shelf life and stability of protein under different conditions. For example, the polypeptides may be employed in a binding affinity study to measure the biological activity of a IL-1 delta counter-structure molecule that has been stored at different temperatures, or produced in different cell types. The proteins also may be used to determine whether biological activity is retained after modification of a IL-1 delta counter-structure molecule (e.g., chemical modification, truncation, mutation, etc.). The binding affinity of the modified IL-1 delta counter-structure molecule is compared to that of an unmodified IL-1 delta counter-structure molecules to detect any adverse impact of the modifications on biological activity of IL-1 delta counter-structure molecules. The biological activity of a IL-1 delta counter-structure molecule thus can be ascertained before it is used in a research study, for example.

Delivery Agents

The polypeptides can be used to deliver diagnostic or therapeutic agents to such cells or cell types found to express IL-1 delta counterestructure molecules on the cell surface in in vitro or in vivo procedures. Therefore, IL-1 delta polypeptide can be attached to a toxin to bind to cells that express IL-1 delta counterestructure molecules on the cell surface and specifically kill these cells. The methodology can be similar to the successful use of an anti-CD72 immunotoxin to treat therapy-refractory B-lineage acute lymphoblastic leukemia in SCID mice (Meyers et al., *Leuk. and Lymph.* 18:119-122).

Detectable (diagnostic) and therapeutic agents that may be attached to a polypeptide include, but are not limited to, toxins, other cytotoxic agents, drugs, radionuclides, chromophores, enzymes that catalyze a calorimetric or fluorometric reaction, and the like, with the particular agent being chosen according to the intended application. Among the toxins are ricin, abrin, diphtheria toxin, *Pseudomonas aeruginosa* exotoxin A, ribosomal inactivating proteins, mycotoxins such as trichothecenes, and derivatives and fragments (e.g., single chains) thereof. Radionuclides suitable for diagnostic use include, but are not limited to, $^{123}$I, $^{131}$I, $^{99m}$Tc, $^{111}$In, and $^{76}$Br. Examples of radionuclides suitable for therapeutic use are $^{131}$I, $^{211}$At, $^{77}$Br, $^{186}$Re, $^{188}$Re, $^{212}$Pb, $^{212}$Bi, $^{109}$Pd, $^{64}$Cu, and $^{67}$Cu.

Such agents may be attached to the polypeptide by any suitable conventional procedure. The polypeptide comprises functional groups on amino acid side chains that can be reacted with functional groups on a desired agent to form covalent bonds, for example. Alternatively, the protein or agent may be derivatized to generate or attach a desired reactive functional group. The derivatization may involve attachment of one of the bifunctional coupling reagents available for attaching various molecules to proteins (Pierce Chemical Company, Rockford, Ill.). A number of techniques for radiolabeling proteins are known. Radionuclide metals may be attached to polypeptides by using a suitable bifunctional chelating agent, for example.

Conjugates comprising polypeptides and a suitable diagnostic or therapeutic agent (preferably covalently linked) are thus prepared. The conjugates are administered or otherwise employed in an amount appropriate for the particular application.

Therapeutic Agents

Another embodiment of the invention relates to therapeutic uses of IL-1 delta. IL-1 ligands play a central role in protection against infection and immune inflammatory responses which includes cellular signal transduction, activating vascular endothelial cells and lymphocytes, induction of inflammatory cytokines, acute phase proteins, hematopoiesis, fever, bone resorption, prostaglandins, metalloproteinases, and adhesion molecules. With the continued increase in the number of known IL-1 family members, a suitable, classification scheme is one based on comparing polypeptide structure as well as function (activation and regulatory properties). Thus, the ligand for IL-1 delta, like IL-1α, IL-1β, and IL-18, would likely be involved in many of the functions noted above as well as promote inflammatory responses and therefore perhaps be involved in the causation and maintenance of inflammatory and/or autoimmune diseases such as rheumatoid arthritis, inflammatory bowel disease, and psoriasis. As such, alterations in the expression and/or activation of IL-1R family members such as IL-1 delta can have profound effects on a plethora of cellular processes, including, but not limited to, activation or inhibition of cell specific responses, proliferation, and inflammatory reactions based on changes in signal transduction.

IL-1 mediated cellular signaling often involves a molecular activation cascade, during which a receptor propagates a ligand-receptor mediated signal by specifically activating intracellular kinases which phosphorylate target substrates, resulting in the activation of the transcription factors NFkB and AP1, the protein kinases Jun N-terminal kinase and p38 map kinase, the enzymes COX-2 leading to prostaglandin production and iNOS leading to nitric oxide production, and inflammation in general. IL-1 delta will likely signal in a similar way. Therefore, administration of IL-1 delta will be useful in circumstances where an increase in nitric oxide, adhesion molecules, JNK and p38 MAP kinase activity, etc, would be helpful, e.g. to stimulate an immune or inflammatory response.

Alternatively, it is possible that IL-1 delta acts as an antagonist of other, active cytokines, in the same way that IL-1ra is an antagonist of the actions of IL-1 alpha and IL-1beta. Therefore, administration of IL-1 delta might have therapeutic application in blocking inflammatory responses, including the activation of transcription factors NFkB and AP1, the protein kinases Jun N-terminal kinase and p38 MAP kinase, the enzymes COX-2 leading to prostaglandin production and iNOS leading to nitric oxide production, and inflammation in general.

Thus, isolated and purified IL-1 delta polypeptides or a fragment thereof of the invention can be useful as therapeutic agents in inhibiting signaling. Soluble IL-1 delta polypeptides can interact with IL-1 delta counterstructures, and inhibit the activation of cells through cell-associated IL-1 delta.

Polypeptides can be introduced into the extracellular environment by well-known means, such as by administering the protein intravenously or coupling it to a monoclonal antibody targeted to a specific cell type, to thereby affect signaling. When used as a therapeutic agent, polypeptides of the invention can be formulated into pharmaceutical compositions according to known methods. The polypeptides can be combined in admixture, either as the sole active material or with other known active materials, with pharmaceutically suitable diluents (e.g., Tris-HCl, acetate, phosphate), preservatives (e.g., Thimerosal, benzyl alcohol, parabens), emulsifiers, solubilizers, adjuvants and/or carriers. Suitable carriers and their formulations are described in Remington's Pharmaceutical Sciences, 16th ed. 1980, Mack Publishing Co. In addition, such compositions can contain the polypeptides complexed with polyethylene glycol (PEG), metal ions, or incorporated into polymeric compounds such as polyacetic acid, polyglycolic acid, hydrogels, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance of polypeptides of the invention.

The dosage of the composition can be readily determined by those of ordinary skill in the art. The amount to be administered and the frequency of administration can be determined empirically and will take into consideration the age and size of the patient being treated, as well as the malady being treated.

Treatment comprises administering the composition by any method familiar to those of ordinary skill in the art, including intravenous, intraperitoneal, intracorporeal injection, intra-articular, intraventricular, intrathecal, intramuscular, subcutaneous, topically, tonsillar, intranasally, intravaginally, and orally. The composition may also be given locally, such as by injection into the particular area, either intramuscularly or subcutaneously.

Rational Drug Design

In addition, IL-1 delta polypeptides can also be used for structure-based design of IL-1 delta inhibitors. Such structure-based design is also known as "rational drug design." The IL-1 delta polypeptides can be three dimensionally analyzed by, for example, X-ray crystallography, nuclear magnetic resonance, or homology modeling, all of which are well known methods. The use of IL-1 delta structural information in molecular modeling software systems to assist in inhibitor design and inhibitor-IL-1 delta interaction is also encompassed by the invention. Such computerassisted modeling and drug design may utilize information such as chemical conformational analysis, electrostatic potential of the molecules, protein folding, etc. For example, most of the design of class-specific inhibitors of metalloproteases has focused on attempts to chelate or bind the catalytic zinc atom. Synthetic inhibitors are usually designed to contain a negatively charged moiety to which is attached a series of other groups designed to fit the specificity pockets of the particular protease. A particular method of the invention comprises analyzing the three dimensional structure of IL-1 delta for likely binding sites of substrates, synthesizing a new molecule that incorporates a predictive reactive site, and assaying the new molecule as described above.

Research Reagents

Another use of the polypeptide of the present invention is as a research tool for studying the biological effects that result from IL-1 delta/IL-1 delta counter-structure interactions on different cell types. Alternatively, if IL-1 delta has antagonist activity, the polypeptide of the present invention could be used as a research tool for studying the biological effects that result from inhibiting the interaction of the IL-1 delta counterstructure with its agonist ligand. Polypeptides also may be employed in in vitro assays for detecting IL-1 delta counter-structure molecules or IL-1 delta polypeptides or the interactions thereof.

IL-1 delta may also be used as a reagent to identify (a) the proteins to which it binds, and which are involved in IL-1 delta signaling, and (b) other proteins with which it might interact which would be involved in signal transduction pathways. These other proteins would then be useful tools to search for other inhibitors of signaling. IL-1 delta could be used by coupling recombinant protein to an affinity matrix, or by using it as a bait in the 2-hybrid system.

The interaction between IL-1 delta polypeptide and its counter-structure enables screening for small molecules that interfere with the IL-1 delta polypeptide/IL-1 delta counter-structure association and therefore either (i) inhibit the activity of IL-1 delta polypeptide or its counter-structure, if IL-1 delta is an agonist, or (ii) allow the binding and signaling activity of the IL-1 delta counterstructure ligand, if IL-1 delta is an antagonist.

To assist in this, the yeast two-hybrid system developed at SUNY (described in U.S. Pat. No. 5,283,173 to Fields et al.) may be used to screen for inhibitors of IL-1 delta as follows. IL-1 delta polypeptide and its counter-structure, or portions thereof responsible for their interaction, may be fused to the Gal 4 DNA binding domain and Gal 4 transcriptional activation domain, respectively, and introduced into a strain that depends on Gal 4 activity for growth on plates lacking histidine. Compounds that prevent growth may be screened in order to identify IL-1 inhibitors. Alternatively, the screen may be modified so that IL-1 delta polypeptide/IL-1 delta polypeptide counter-structure interaction inhibits growth, so that inhibition of the interaction allows growth to occur.

Another in vitro approach to screening for IL-1 delta inhibition would be to immobilize one of the components (either IL-1 delta polypeptide or its counter-structure) in wells of a microtiter plate, and to couple an easily detected indicator to the other component. An inhibitor of the interaction is identified by the absence of the detectable indicator from the well.

In addition, IL-1 delta polypeptides according to the invention are useful for the structure-based design of an IL-1 delta inhibitor. Such a design would comprise the steps of determining the three-dimensional structure of the IL-1 delta polypeptide, analyzing the three-dimensional structure for the likely binding sites of substrates, synthesizing a molecule that incorporates a predictive reactive site, and determining the inhibiting activity of the molecule.

IL-1 delta DNA, IL-1 delta polypeptides, and antibodies against IL-1 delta polypeptides can be used as reagents in a variety of research protocols. A sample of such research protocols are given in Sambrook et al. *Molecular Cloning: A Laboratory Manual*, 2 ed. Vol. 1-3, Cold Spring Harbor Laboratory Press, (1989). For example, these reagents can serve as markers for cell specific or tissue specific expression of RNA or proteins. Similarly, these reagents can be used to investigate constituitive and transient expression of IL-1 delta RNA or polypeptides. IL-1 delta DNA can be used to determine the chromosomal location of sequences related to IL-1 delta DNA and to map genes in relation to this chromosomal location. IL-1 delta DNA can also be used to examine genetic heterogeneity and heredity, through the use of techniques such as genetic fingerprinting, as well as to identify risks associated with genetic disorders. IL-1 delta DNA can be further used to identify additional genes related to IL-1 delta DNA and to establish evolutionary trees based on the comparison of sequences. IL-1 delta DNA and polypeptides can be used to select for those genes or proteins that are homologous to IL-1 delta DNA or polypeptides through positive screening procedures, such as Southern blotting and immunoblotting, and through negative screening procedures, such as subtraction.

Molecular Weight, Isoelectric Point Markers

The polypeptides of the present invention can be subjected to fragmentation into smaller peptides by chemical and enzymatic means, and the peptide fragments so produced can be used in the analysis of other proteins or polypeptides. For example, such peptide fragments can be used as peptide molecular weight markers, peptide isoelectric point markers, or in the analysis of the degree of peptide fragmentation. Thus, the invention also includes these polypeptides and peptide fragments, as well as kits to aid in the determination of the apparent molecular weight and isoelectric point of an unknown protein and kits to assess the degree of fragmentation of an unknown protein.

Although all methods of fragmentation are encompassed by the invention, chemical fragmentation is a preferred embodiment, and includes the use of cyanogen bromide to cleave under neutral or acidic conditions such that specific cleavage occurs at methionine residues (E. Gross, *Methods in Enz.* 11:238-255, 1967). This can further include additional steps, such as a carboxymethylation step to convert cysteine residues to an unreactive species.

Enzymatic fragmentation is another preferred embodiment, and includes the use of a protease such as Asparaginylendo-peptidase, Arginylendo-peptidase, *Achromobacter* protease I, Trypsin, *Staphlococcus aureus* V8 protease, Endoproteinase Asp-N, or Endoproteinase Lys-C under conventional conditions to result in cleavage at specific amino acid residues. Asparaginylendo-peptidase can cleave specifically on the carboxyl side of the asparagine residues present within the polypeptides of the invention. Arginylendo-peptidase can cleave specifically on the carboxyl side of the arginine residues present within these polypeptides. *Achromobacter* protease I can cleave specifically on the carboxyl side of the lysine residues present within the polypeptides (Sakiyama and Nakat, U.S. Pat. No. 5,248,599; T. Masaki et al., *Biochim. Biophys. Acta* 660:44-50, 1981; T. Masaki et al., *Biochim. Biophys. Acta* 660:51-55, 1981). Trypsin can cleave specifically on the carboxyl side of the arginine and lysine residues present within polypeptides of the invention. Enzymatic fragmentation may also occur with a protease that cleaves at multiple amino acid residues. For example, *Staphlococcus aureus* V8 protease can cleave specifically on the carboxyl side of the aspartic and glutamic acid residues present within polypeptides (D. W. Cleveland, *J. Biol. Chem.* 3:1102-1106, 1977). Endoproteinase Asp-N can cleave specifically on the amino side of the asparagine residues present within polypeptides. Endoproteinase Lys-C can cleave specifically on the carboxyl side of the lysine residues present within polypeptides of the invention. Other enzymatic and chemical treatments can likewise be used to specifically fragment these polypeptides into a unique set of specific peptides.

Of course, the peptides and fragments of the polypeptides of the invention can also be produced by conventional recombinant processes and synthetic processes well known in the art. With regard to recombinant processes, the polypeptides and peptide fragments encompassed by invention can have variable molecular weights, depending upon the host cell in which they are expressed. Glycosylation of polypeptides and peptide fragments of the invention in various cell types can result in variations of the molecular weight of these pieces, depending upon the extent of modification. The size of these pieces can be most heterogeneous with fragments of polypeptide derived from the extracellular portion of the polypeptide. Consistent polypeptides and peptide fragments can be obtained by using polypeptides derived entirely from the transmembrane and cytoplasmic regions, pretreating with N-glycanase to remove glycosylation, or expressing the polypeptides in bacterial hosts.

The molecular weight of these polypeptides can also be varied by fusing additional peptide sequences to both the amino and carboxyl terminal ends of polypeptides of the invention. Fusions of additional peptide sequences at the amino and carboxyl terminal ends of polypeptides of the invention can be used to enhance expression of these polypeptides or aid in the purification of the protein. In addition, fusions of additional peptide sequences at the amino and carboxyl terminal ends of polypeptides of the invention will alter some, but usually not all, of the fragmented peptides of the polypeptides generated by enzymatic or chemical treatment. Of course, mutations can be introduced into polypeptides of the invention using routine and known techniques of molecular biology. For example, a mutation can be designed so as to eliminate a site of proteolytic cleavage by a specific enzyme or a site of cleavage by a specific chemically induced fragmentation procedure. The elimination of the site will alter the peptide fingerprint of polypeptides of the invention upon fragmentation with the specific enzyme or chemical procedure.

The polypeptides and the resultant fragmented peptides can be analyzed by methods including sedimentation, electrophoresis, chromatography, and mass spectrometry to determine their molecular weights. Because the unique amino acid sequence of each piece specifies a molecular weight, these pieces can thereafter serve as molecular weight markers using such analysis techniques to assist in the determination of the molecular weight of an unknown protein, polypeptides or fragments thereof. The molecular weight markers of the invention serve particularly well as molecular weight markers for the estimation of the apparent molecular weight of proteins that have similar apparent molecular weights and, consequently, allow increased accuracy in the determination of apparent molecular weight of proteins.

When the invention relates to the use of IL-1 delta polypeptide fragments and fragmented peptide molecular weight markers, those markers are preferably at least 10 amino acids in size. More preferably, these fragmented peptide molecular weight markers are between 10 and 100 amino acids in size. Even more preferable are fragmented peptide molecular weight markers between 10 and 50 amino acids in size and especially between 10 and 35 amino acids in size. Most preferable are fragmented peptide molecular weight markers between 10 and 20 amino acids in size.

Among the methods for determining molecular weight are sedimentation, gel electrophoresis, chromatography, and mass spectrometry. A particularly preferred embodiment is denaturing polyacrylamide gel electrophoresis (U. K. Laemmli, *Nature* 227:680-685, 1970). Conventionally, the method uses two separate lanes of a gel containing sodium dodecyl sulfate and a concentration of acrylamide between 6-20%. Proteins on the gel can be visualized using a conventional staining procedure. The ability to simultaneously resolve the marker and the sample under identical conditions allows for increased accuracy. It is understood, of course, that many different techniques can be used for the determination of the molecular weight of an unknown protein using polypeptides of the invention, and that this embodiment in no way limits the scope of the invention.

Each unglycosylated polypeptide or fragment thereof has a pI that is intrinsically determined by its unique amino acid sequence (which pI can be estimated by the skilled artisan using any of the computer programs designed to predict pI values currently available, calculated using any well-known amino acid pKa table, or measured empirically). Therefore these polypeptides and fragments thereof can serve as specific markers to assist in the determination of the isoelectric point of an unknown protein, polypeptide, or fragmented peptide using techniques such as isoelectric focusing. These polypeptide or fragmented peptide markers serve particularly well for the estimation of apparent isoelectric points of unknown proteins that have apparent isoelectric points close to that of the polypeptide or fragmented peptide markers of the invention.

The technique of isoelectric focusing can be further combined with other techniques such as gel electrophoresis to simultaneously separate a protein on the basis of molecular weight and charge. The ability to simultaneously resolve these polypeptide or fragmented peptide markers and the unknown protein under identical conditions allows for increased accuracy in the determination of the apparent isoelectric point of the unknown protein. This is of particular interest in techniques, such as two dimensional electrophoresis (T. D. Brock and M. T. Madigan, *Biology of Microorganisms* 76-77 (Prentice Hall, 6d ed. 1991)), where the nature of the procedure dictates that any markers should be resolved simultaneously with the unknown protein. In addition, with such methods, these polypeptides and fragmented peptides thereof can assist in the determination of both the isoelectric point and molecular weight of an unknown protein or fragmented peptide.

Polypeptides and fragmented peptides can be visualized using two different methods that allow a discrimination between the unknown protein and the molecular weight markers. In one embodiment, the polypeptide and fragmented peptide molecular weight markers of the invention can be visualized using antibodies generated against these markers and conventional immunoblotting techniques. This detection is performed under conventional conditions that do not result in the detection of the unknown protein. It is understood that it may not be possible to generate antibodies against all polypeptide fragments of the invention, since small peptides may not contain immunogenic epitopes. It is further understood that not all antibodies will work in this assay; however, those antibodies which are able to bind polypeptides and fragments of the invention can be readily determined using conventional techniques.

The unknown protein is also visualized by using a conventional staining procedure. The molar excess of unknown protein to polypeptide or fragmented peptide molecular weight markers of the invention is such that the conventional staining procedure predominantly detects the unknown protein. The level of these polypeptide or fragmented peptide molecular weight markers is such as to allow little or no detection of these markers by the conventional staining method. The preferred molar excess of unknown protein to polypeptide molecular weight markers of the invention is between 2 and 100,000 fold. More preferably, the preferred molar excess of unknown protein to these polypeptide molecular weight markers is between 10 and 10,000 fold and especially between 100 and 1,000 fold.

It is understood of course that many techniques can be used for the determination and detection of molecular weight and isoelectric point of an unknown protein, polypeptides, and fragmented peptides thereof using these polypeptide molecular weight markers and peptide fragments thereof and that these embodiments in no way limit the scope of the invention.

In another embodiment, the analysis of the progressive fragmentation of the polypeptides of the invention into specific peptides (D. W. Cleveland et al., *J. Biol. Chem.* 252:1102-1106, 1977), such as by altering the time or temperature of the fragmentation reaction, can be used as a control for the extent of cleavage of an unknown protein. For example, cleavage of the same amount of polypeptide and unknown protein under identical conditions can allow for a direct comparison of the extent of fragmentation. Conditions that result in the complete fragmentation of the polypeptide can also result in complete fragmentation of the unknown protein.

Thus, in a preferred embodiment of the invention, the IL-1 delta polypeptides may be used as molecular weight markers to estimate the apparent molecular weight of a sample protein by gel electrophoresis. An isolated and purified mouse IL-1 delta polypeptide molecular weight marker according to the invention (SEQ ID NO:2) has a molecular weight of approximately 17,124 Daltons, in the absence of glycosylation. Therefore, the IL-1 delta polypeptide molecular weight marker serves particularly well as a molecular weight marker for the estimation of the apparent molecular weight of sample proteins that have apparent molecular weights close to 17,124 Daltons and allows an increased accuracy in the determination of apparent molecular weight of proteins that have apparent molecular weights close to 17,124 Daltons.

Another preferred embodiment of the invention is the use of IL-1 delta fragments, generated by chemical fragmentation of IL-1 delta polypeptide, as molecular weight markers to estimate the apparent molecular weight of a sample protein by gel electrophoresis. Isolated and purified IL-1 delta polypeptide can be treated with cyanogen bromide under conventional conditions that result in fragmentation of the IL-1 delta polypeptide by specific hydrolysis on the carboxyl side of the methionine residues within the IL-1 delta polypeptide (E. Gross, *Methods in Enz.* 11:238-255, 1967). Due to the unique amino acid sequence of the IL-1 delta polypeptide, the fragmentation of IL-1 delta polypeptide with cyanogen bromide generates a unique set of IL-1 delta fragmented peptide molecular weight markers, as noted above.

The unique set of IL-1 delta fragmented peptide molecular weight markers generated by treatment of mouse IL-1 delta polypeptide with cyanogen bromide comprises 4-fragmented peptides of at least 10 amino acids in size. The peptide encoded by amino acids 3-12 of SEQ ID NO:2 has a molecular weight of approximately 1,095 Daltons. The peptide encoded by amino acids 13-87 of SEQ ID NO:2 has a molecular weight of approximately 7,871 Daltons. The peptide encoded by amino acids 88-106 of SEQ ID NO:2 has a molecular weight of approximately 2,340 Daltons. The peptide encoded by amino acids 107-156 of SEQ ID NO:2 has a molecular weight of approximately 5,609 Daltons. Therefore, IL-1 delta fragmented peptide molecular weight markers have molecular weights of approximately 1,095; 7,871; 2,340; and 5,609 Daltons.

The IL-1 delta fragmented peptide molecular weight markers, together with a sample protein, can be resolved, as described above, by denaturing polyacrylamide gel electrophoresis. The IL-1 delta fragmented peptide molecular weight markers serve particularly well as molecular weight markers for the estimation of the apparent molecular weight of sample proteins that have apparent molecular weights close to 1,095; 7,871; 2,340; or 5,609 Daltons. It is understood of course that the unique amino acid sequence of human IL-1 delta polypeptide (SEQ ID NO:4) can similarly be used to generate a unique set of human IL-1 delta fragmented peptide molecular weight markers. The fragmented sizes can be readily determined using available computer programs.

The extent of fragmentation of either the murine or human IL-1 delta polypeptide is further used as a control to determine the conditions expected for complete fragmentation of the sample protein. It is understood of course that many chemicals could be used to fragment IL-1 delta polypeptides and that this embodiment in no way limits the scope of the invention.

In another embodiment, unique sets of IL-1 delta fragmented peptide molecular weight markers can be generated from IL-1 delta polypeptide using enzymes that cleave the polypeptide at specific amino acid residues. Due to the unique nature of the amino acid sequence of the IL-1 delta polypeptide, cleavage at different amino acid residues will result in the generation of different sets of fragmented peptide molecular weight markers.

For example, an isolated and purified IL-1 delta polypeptide can be treated with *Achromobacter* protease I under conventional conditions, as noted above, to result in fragmentation of the IL-1 delta polypeptide. Due to the unique amino acid sequence of the IL-1 delta polypeptide, the fragmentation of IL-1 delta polypeptide molecular weight markers with *Achromobacter* protease I generates a unique set of IL-1 delta fragmented peptide molecular weight markers. The distribution of lysine residues determines the number of amino acids in each peptide and the unique amino acid composition of each peptide determines its molecular weight.

The unique set of IL-1 delta fragmented peptide molecular weight markers generated by treatment of mouse IL-1 delta polypeptide with *Achromobacter* protease I comprises 5 fragmented peptides of at least 10 amino acids in size. The generation of 5 fragmented peptides with this enzyme treatment of the IL-1 delta polypeptide, compared to 4 fragmented peptides with cyanogen bromide treatment of the IL-1 delta polypeptide, clearly illustrates that both the size and number of the fragmented peptide molecular weight markers will vary depending upon the fragmentation treatment utilized to fragment the IL-1 delta polypeptide. In addition, fragmentation of human IL-1 delta polypeptide (SEQ ID NO:4) will result in unique sets of fragmented peptides, dictated by the amino acid sequence of the IL-1 delta polypeptide.

As to the specific fragments, the peptide encoded by amino acids 1-13 of SEQ ID NO:2 has a molecular weight of approximately 1,485 Daltons. The peptide encoded by amino acids 19-36 of SEQ ID NO:2 has a molecular weight of approximately 1,989 Daltons. The peptide encoded by amino acids 40-75 of SEQ ID NO:2 has a molecular weight of approximately 3,612 Daltons. The peptide encoded by amino acids 81-94 of SEQ ID NO:2 has a molecular weight of approximately 1,588 Daltons. The peptide encoded by amino acids 98-156 of SEQ ID NO:2 has a molecular weight of approximately 6,813 Daltons.

Therefore, cleavage of the IL-1 delta polypeptide by enzymatic treatment with *Achromobacter* protease I generates a unique set of IL-1 delta fragments having molecular weights of approximately 1,485; 1,989; 3,612; 1,588; and 6,813 Daltons.

It is understood of course that the unique amino acid sequence of human IL-1 delta polypeptide (SEQ ID NO:4) can similarly be used to generate a unique set of human IL-1 delta fragmented peptide molecular weight markers. The fragmented sizes can be readily determined using available computer programs. Once again, the IL-1 delta fragmented peptide molecular weight markers, together with a sample protein, can be resolved by denaturing polyacrylamide gel electrophoresis by conventional means.

Finally, as to the kits that are encompassed by the invention, the constituents of such kits can be varied, but typically contain the polypeptide and fragmented peptide molecular weight markers. Also, such kits can contain the polypeptides wherein a site necessary for fragmentation has been removed. Furthermore, the kits can contain reagents for the specific cleavage of the polypeptide and the unknown protein by chemical or enzymatic cleavage. Kits can further contain antibodies directed against polypeptides or fragments thereof of the invention.

Identification of Unknown Proteins

As set forth above, a polypeptide or peptide fingerprint can be entered into or compared to a database of known proteins to assist in the identification of the unknown protein using mass spectrometry (W. J. Henzel et al., Proc. Natl. Acad. Sci. USA 90:5011-5015, 1993; D. Fenyo et al., Electrophoresis 19:998-1005, 1998). A variety of computer software programs to facilitate these comparisons are accessible via the Internet, such as Protein Prospector (Internet site: prospector.uscf.edu), Multildent (Internet site: www.expasy.ch/sprot/multiident.html), PeptideSearch (Internet site: www.mann.embl-heiedelberg.de . . . deSearch/FR PeptideSearch Form.html), and ProFound (Internet site: www.chait sgi.Rockefeller.edu/cgi bin/prot id frag.html). These programs allow the user to specify the cleavage agent and the molecular weights of the fragmented peptides within a designated tolerance. The programs compare observed molecular weights to predicted peptide molecular weights derived from sequence databases to assist in determining the identity of the unknown protein.

In addition, a polypeptide or peptide digest can be sequenced using tandem mass spectrometry (MS/MS) and the resulting sequence searched against databases (J. K. Eng, et al., J. Am. Soc. Mass Spec. 5:976-989 (1994); M. Mann and M. Wilm, Anal. Chem. 66:4390-4399 (1994); J. A. Taylor and R. S. Johnson, Rapid Comm. Mass Spec. 11:1067-1075 (1997)). Searching programs that can be used in this process exist on the Internet, such as Lutefisk 97 (Internet site www.Isbc.com:70/Lutefisk97.html), and the Protein Prospector, Peptide Search and ProFound programs described above.

Therefore, adding the sequence of a gene and its predicted protein sequence and peptide fragments to a sequence database can aid in the identification of unknown proteins using mass spectrometry.

Antibodies

Antibodies that are immunoreactive with the polypeptides of the invention are provided herein. Such antibodies specifically bind to the polypeptides via the antigen-binding sites of the antibody (as opposed to non-specific binding). Thus, the polypeptides, fragments, variants, fusion proteins, etc., as set forth above may be employed as immunogens in producing antibodies immunoreactive therewith. More specifically, the polypeptides, fragment, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, *Immuno Biology* 3:9 (Garland Publishing Inc., 2nd ed. 1996)). Because folded proteins have complex surfaces, the number of epitopes available is quite numerous; however, due to the conformation of the protein and steric hinderances, the number of antibodies that actually bind to the epitopes is less than the number of available epitopes (C. A. Janeway, Jr. and P. Travers, *Immuno Biology* 2:14 (Garland Publishing Inc., 2nd ed. 1996)). Epitopes may be identified by any of the methods known in the art.

Thus, one aspect of the present invention relates to the antigenic epitopes of the polypeptides of the invention. Such epitopes are useful for raising antibodies, in particular monoclonal antibodies, as described in detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides of the invention, whether the epitopes have been isolated or remain part of the polypeptides, both polyclonal and monoclonal antibodies may be prepared by conventional techniques as described below.

In this aspect of the invention, IL-1 delta and peptides based on the amino acid sequence of IL-1 delta, can be utilized to prepare antibodies that specifically bind to IL-1 delta. The term "antibodies" is meant to include polyclonal antibodies, monoclonal antibodies, fragments thereof, such as F(ab')2 and Fab fragments, as well as any recombinantly produced binding partners. Antibodies are defined to be specifically binding if they bind IL-1 delta polypeptide with a $K_a$ of greater than or equal to about $10^7$ $M^{-1}$. Affinities of binding partners or antibodies can be readily determined using conventional techniques, for example those described by Scatchard et al., *Ann. N.Y Acad. Sci.*, 51:660 (1949).

Polyclonal antibodies can be readily generated from a variety of sources, for example, horses, cows, goats, sheep, dogs, chickens, rabbits, mice, or rats, using procedures that are well known in the art. In general, purified IL-1 delta or a peptide based on the amino acid sequence of IL-1 delta polypeptide that is appropriately conjugated is administered to the host animal typically through parenteral injection. The immunogenicity of IL-1 delta polypeptide can be enhanced through the use of an adjuvant, for example, Freund's complete or incomplete adjuvant. Following booster immunizations, small samples of serum are collected and tested for reactivity to IL-1 delta polypeptide. Examples of various assays useful for such determination include those described in *Antibodies: A Laboratory Manual*, Harlow and Lane (eds.), Cold Spring Harbor Laboratory Press, 1988; as well as procedures, such as countercurrent immuno-electrophoresis (CIEP), radioimmunoassay, radio-immunoprecipitation, enzyme-linked immunosorbent assays (ELISA), dot blot assays, and sandwich assays. See U.S. Pat. Nos. 4,376,110 and 4,486,530.

Monoclonal antibodies can be readily prepared using well known procedures. See, for example, the procedures described in U.S. Pat. Nos. RE 32,011, 4,902,614, 4,543,439, and 4,411,993; Monoclonal Antibodies, Hybridomas: *A New Dimension in Biological Analyses*, Plenum Press, Kennett, McKearn, and Bechtol (eds.), 1980. Briefly, the host animals, such as mice, are injected intraperitoneally at least once and preferably at least twice at about 3 week intervals with isolated and purified IL-1 delta or conjugated IL-1 delta peptide, optionally in the presence of adjuvant. Mouse sera are then assayed by conventional dot blot technique or antibody capture (ABC) to determine which animal is best to fuse. Approximately two to three weeks later, the mice are given an intravenous boost of IL-1 delta or conjugated IL-1 delta peptide. Mice are later sacrificed and spleen cells fused with commercially available myeloma cells, such as Ag8.653 (ATCC), following established protocols. Briefly, the myeloma cells are washed several times in media and fused to mouse spleen cells at a ratio of about three spleen cells to one myeloma cell. The fusing agent can be any suitable agent used in the art, for example, polyethylene glycol (PEG). Fusion is plated out into plates containing media that allows for the selective growth of the fused cells. The fused cells can then be allowed to grow for approximately eight days. Supernatants from resultant hybridomas are collected and added to a plate that is first coated with goat anti-mouse Ig. Following washes, a label, such as $^{125}$I-IL-1 delta, is added to each well followed by incubation. Positive wells can be subsequently detected by autoradiography. Positive clones can be grown in bulk culture and supernatants are subsequently purified over a Protein A column (Pharmacia).

The monoclonal antibodies of the invention can be produced using alternative techniques, such as those described by Alting-Mees et al., "Monoclonal Antibody Expression Libraries: A Rapid Alternative to Hybridomas", *Strategies in Molecular Biology* 3:1-9 (1990), which is incorporated herein by reference. Similarly, binding partners can be constructed using recombinant DNA techniques to incorporate the variable regions of a gene that encodes a specific binding antibody. Such a technique is described in Larrick et al., *Biotechnology*, 7:394 (1989).

Antigen-binding fragments of such antibodies, which may be produced by conventional techniques, are also encompassed by the present invention. Examples of such fragments include, but are not limited to, Fab and F(ab')$_2$ fragments. Antibody fragments and derivatives produced by genetic engineering techniques are also provided.

The monoclonal antibodies of the present invention include chimeric antibodies, e.g., humanized versions of murine monoclonal antibodies. Such humanized antibodies may be prepared by known techniques, and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332:323, 1988), Liu et al. (*PNAS* 84:3439, 1987), Larrick et al. (*Bio/Technology* 7:934, 1989), and Winter and Harris (*TIPS* 14:139, May, 1993). Procedures to generate antibodies transgenically can be found in GB 2,272,440, U.S. Pat. Nos. 5,569,825 and 5,545,806 and related patents claiming priority therefrom, all of which are incorporated by reference herein.

Uses Thereof

The antibodies of the invention can be used in assays to detect the presence of the polypeptides or fragments of the invention, either in vitro or in vivo. Due to the RNA expression pattern of IL-1 delta, it is expected that IL-1 delta polypeptides will be expressed in lymph node, thymus, tonsil, brain, placenta, lung, skeletal muscle, prostate, and testis cells and tissues. Antibodies against IL-1 delta polypeptides can be used to detect lymph node, thymus, tonsil, brain, placenta, lung, skeletal muscle, prostate, and testis tissue and cell types by convention immunohistochemical methods. The antibodies also may be employed in purifying polypeptides or fragments of the invention by immunoaffinity chromatography.

Those antibodies that additionally can block binding of the polypeptides of the invention to IL-1 delta counter-structure molecules may be used to effect a biological activity that results from such binding. The antibodies may either (i) inhibit the activity of IL-1 delta polypeptide, if IL-1 delta is an agonist, or (ii) allow the binding and signaling activity of the IL-1 delta counterstructure ligand, if IL-1 delta is an antagonist. For example, activation of the transcription factors NFkB and AP1, the protein kinases Jun N-terminal kinase and p38 map, the enzymes COX-2 leading to prostaglandin production and iNOS leading to nitric oxide production, and inflammation in general may be inhibited. Such blocking antibodies may be identified using any suitable assay procedure, such as by testing antibodies for the ability to inhibit binding of IL-1 delta polypeptides to certain cells expressing IL-1 delta counter-structure molecules. Alternatively, blocking antibodies may be identified in assays for the ability to inhibit a biological effect that results from binding of IL-1 delta counter-structure molecules to target cells. Antibodies may be assayed for the ability to inhibit IL-1 delta counter-structure molecules-mediated lysis of cells, for example.

Such an antibody may be employed in an in vitro procedure, or administered in vivo to inhibit a biological activity mediated by the entity that generated the antibody. Disorders caused or exacerbated (directly or indirectly) by the interaction of IL-1 delta counter-structure molecules with cell surface (binding partner) receptor thus may be treated. A therapeutic method involves in vivo administration of a blocking antibody to a mammal in an amount effective in inhibiting a IL-1 delta counter-structure molecule-mediated biological activity. Monoclonal antibodies are generally preferred for use in such therapeutic methods. In one embodiment, an antigen-binding antibody fragment is employed.

Compositions comprising an antibody that is directed against IL-1 delta polypeptides, and a physiologically acceptable diluent, excipient, or carrier, are provided herein. Suitable components of such compositions are as described above for compositions containing IL-1 delta polypeptides.

Also provided herein are conjugates comprising a detectable (e.g., diagnostic) or therapeutic agent, attached to the antibody. Examples of such agents are presented above. The conjugates find use in in vitro or in vivo procedures.

The references cited herein are incorporated by reference herein in their entirety.

The embodiments within the specification and the following examples provide an illustration of embodiments of the invention and should not be construed to limit the scope of the invention. The skilled artisan recognizes many other embodiments are encompassed by the claimed invention.

EXAMPLE 1

Recombinant Expression of Human IL-1 Delta

A full length human IL-1 delta expression construct was generated in the following manner. IL-17 DNA encoding IL-1 delta polypeptide was cloned in frame, either without a tag or with a C-terminal FLAG/polyHis tag, between the SalI and NotI sites of the expression vector pDC412. The protein was produced by transfection into COS cells. Human IL-1 delta was secreted with moderate efficiency from transfected COS or CV-1/EBNA cells.

EXAMPLE 2

Human IL-1 Delta RNA Expression

Expression of human IL-1 delta mRNA was analyzed using 3 Clontech multiple tissue cDNA panels via a nested PCR approach. The three panels used were:
1. Human Panel I (Cat.# K1420-1) Contains heart, brain, placenta, lung, liver, skeletal muscle, kidney, and pancreas first strand cDNAs.
2. Human panel II (Cat.# K1421-1) Contains spleen, thymus, prostate, testis, ovary, small intestine, colon and peripheral blood leukocyte first strand cDNAs.
3. Human Immune Panel (Cat.# K1426-1) Contains spleen, lymph node, thymus, tonsil, bone marrow, fetal liver, and peripheral blood leukocyte first strand cDNAs.

Analysis was performed by an initial round of PCR followed by a second round of PCR using nested primers.

FIRST ROUND: Primers: 5' sense=BRR464.26 (gust upstream of coding region, in 5' UTR)

3' antisense=BRR453.26 (within coding region, near 3' end)

BRR464.26 5' GGGAGTCTACACCCTGTGGAGCTCAA 3' (SEQ ID NO:8)

BRR453.26 5' CTGCTGGMGTAGMGTCTGTGATGG 3' (SEQ ID NO:9)

Reaction conditions (per 50 ul reaction):
5 ul each 1 st strand cDNA (or 5 ul H20 for negative control or 100 ng human genomic DNA), 12.5 pmol each primer −200 uM each dNTP, 0.5 ul of a 16:1 mixture of KlenTaq1 and Vent polymerases, 50 mM Tris-HCl, pH 9.2-3.5 mM $MgCl_2$, 16 mM $(NH_4)_2SO_4$, and 150 ug/ml BSA Cycling parameters:
1 cycle 98° C., 3 min; 58° C., 45 sec; 72° C., 45 sec
28 cycles 98° C., 45 sec; 58° C., 45 sec; 72° C., 45 sec
1 cycle 98° C., 45 sec; 58° C., 45 sec; 72° C., 45 sec SECOND ROUND: Reactions from first round were diluted 1:50 in TE and 1 µl of each dilution amplified with nested primers.

Primers: 5' sense=BRR463.30 (spans initiating ATG; downstream of and overlapping first sense primer). 3' antisense=BRR462.28 (within coding region, near 3' end; downstream of first antisense primer).

BRR463.30 5' GGAGCTCMGATGGTCCTGAGTGGGGCGCT 3' (SEQ ID NO:10)

BRR462.28 5' GCATTCCAGCCACCATTCTCGGGAAGCT 3' (SEQ ID NO:11)

Reaction conditions and cycling parameters were identical to that of the first round. 10 µl of each reaction from first and second round PCRs were separated by electrophoresis on 1.2% agarose gels. Products were visualized by UV light following staining with ethidium bromide. Expression was detected in lymph node, thymus, tonsil, brain, placenta, lung, skeletal muscle, prostate, and testis.

EXAMPLE 3

Human IL-1 Delta Polypeptide Purification

The poly His tag is used to bind the recombinant protein to Nickel-NTA resin (manufactured by Qiagen, http://www.giagen.com/) according to the manufacturer's instructions. The resin is washed with 30 column volumes of 20 mM NaPO4 pH 7.4+300 mM NaCl+5 mM Imidazole. The recombinant protein is then eluted using increasing concentrations of Imidazole. Initially a gradient of 5-20 mM Imidazole 20 mM NaPO4 pH 7.4+300 mM NaCl is used, followed by 20 mM Imidazole 20 mM NaPO4 pH 7.4+300 mM NaCl, followed by a gradient of 20-100 mM Imidazole 20 mM NaPO4 pH 7.4+300 mM NaCl, followed by 100 mM Imidazole 20 mM NaPO4 pH 7.4+300 mM NaCl, followed by 500 mM Imidazole 20 mM NaPO4 pH 7.4+300 mM NaCl. Fractions are collected and analysed by SDS-PAGE to identify those containing the recombinant protein.

What is claimed is:

1. An isolated nucleic acid molecule consisting of the nucleic acid sequence of SEQ ID NO:3.

* * * * *